(12) United States Patent
Cui et al.

(10) Patent No.: US 11,160,875 B2
(45) Date of Patent: Nov. 2, 2021

(54) THERAPEUTIC NANOFIBER HYDROGELS FOR LOCAL TREATMENT OF BRAIN-RELATED DISEASES

(71) Applicant: THE JOHNS HOPKINS UNIVERSITY, Baltimore, MD (US)

(72) Inventors: Honggang Cui, Lutherville, MD (US); Alfredo Quinones-Hinojosa, Bel Air, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 296 days.

(21) Appl. No.: 15/736,818

(22) PCT Filed: Jun. 16, 2016

(86) PCT No.: PCT/US2016/037781
§ 371 (c)(1),
(2) Date: Dec. 15, 2017

(87) PCT Pub. No.: WO2016/205459
PCT Pub. Date: Dec. 22, 2016

(65) Prior Publication Data
US 2018/0360987 A1 Dec. 20, 2018

Related U.S. Application Data

(60) Provisional application No. 62/180,264, filed on Jun. 16, 2015.

(51) Int. Cl.
*A61K 47/69* (2017.01)
*A61K 47/64* (2017.01)
*A61P 35/00* (2006.01)
*A61K 31/196* (2006.01)
*A61K 31/337* (2006.01)
*A61K 31/407* (2006.01)
*B82Y 5/00* (2011.01)

(52) U.S. Cl.
CPC ........ *A61K 47/6903* (2017.08); *A61K 31/196* (2013.01); *A61K 31/337* (2013.01); *A61K 31/407* (2013.01); *A61K 47/64* (2017.08); *A61P 35/00* (2018.01); *B82Y 5/00* (2013.01)

(58) Field of Classification Search
None
See application file for complete search history.

(56) References Cited

U.S. PATENT DOCUMENTS

2005/0064392 A1* 3/2005 Hoxie ............... C07H 21/04
435/5
2014/0090105 A1* 3/2014 Huang ............... C12N 15/8285
800/279

FOREIGN PATENT DOCUMENTS

WO 2012-166705 A2 12/2012
WO WO 2014066002 * 5/2014
WO WO 2014055810 * 4/2016

OTHER PUBLICATIONS

Liu "Generation of Carcinoembryonic Antigen (CEA)-Specific T-Cell Responses in HLA-A*0201 and HLA-A*2402 Late-Stage Colorectal Cancer Patients after Vaccination with Dendritic Cells Loaded with CEA Peptides" CCR 10:2645-2651 (Year: 2004).*
Uniprot "F4K519" accessed from uniprot on Feb. 25, 2020 (Year: 2020).*
Shridas "Human Dolichol Kinase, a Polytopic Endoplasmic Reticulum Membrane Protein with a Cytoplasmically Oriented CTP-binding Site" JBC 281 (42):31696-31704 (Year: 2006).*
Peptide "Results" accessed from peptide2.com on Feb. 25, 2020 (Year: 2020).*
Shu, C. et al., "Synergistic dual-targeting hydrogel improves targeting and anticancer effect of Taxol in vitro and in vivo." Chemical Communications, 2014, vol. 50, No. 97, pp. 15423-15426 and supplementary information.
Gao, Y. et al., "Enzyme-instructed molecular self-assembly confers nanofibers and a supramolecular hydrogel of taxol derivative." Journal of the American Chemical Society, 2009, vol. 131, No. 38, pp. 13576-13577.
Tian, R. et al., "Drug delivery with nanospherical supramolecular cell penetrating peptide-taxol conjugates containing a high drug loading." Journal of Colloid and Interface Science, Apr. 29, 2015 (Online), vol. 453, pp. 15-20.
Lin, R. et al., "Supramolecular filaments containing a fixed 41% paclitaxel loading." Chemical Communications, 2013, vol. 49, No. 43, pp. 4968-4970.
Zhou et al., "Self-assembled peptide-based hydrogels as scaffolds for anchorage-dependent cells." Biomaterials. May 2009;30(13):2523-30.

* cited by examiner

*Primary Examiner* — Adam Weidner
(74) *Attorney, Agent, or Firm* — Casimir Jones S.C.; Thomas Isenbarger

(57) ABSTRACT

The present invention provides compositions comprising at least one biologically active agent (D) chemically conjugated to a peptide or oligopeptide with overall hydrophilicity (Pep). In some embodiments, the composition comprises D-Pep wherein the biologically active agents are linked to the Pep molecule via an chemical linker, such as amino acid linker. These compositions can be mixed with the other compositions to provide mixtures of nanofiber hydrogel structures that also can be used to locally deliver biologically active agents to tissues of interest. The methods and compositions disclosed herein are useful for sustained drug release when administered in situ to the tissue of interest.

21 Claims, 19 Drawing Sheets
Specification includes a Sequence Listing.

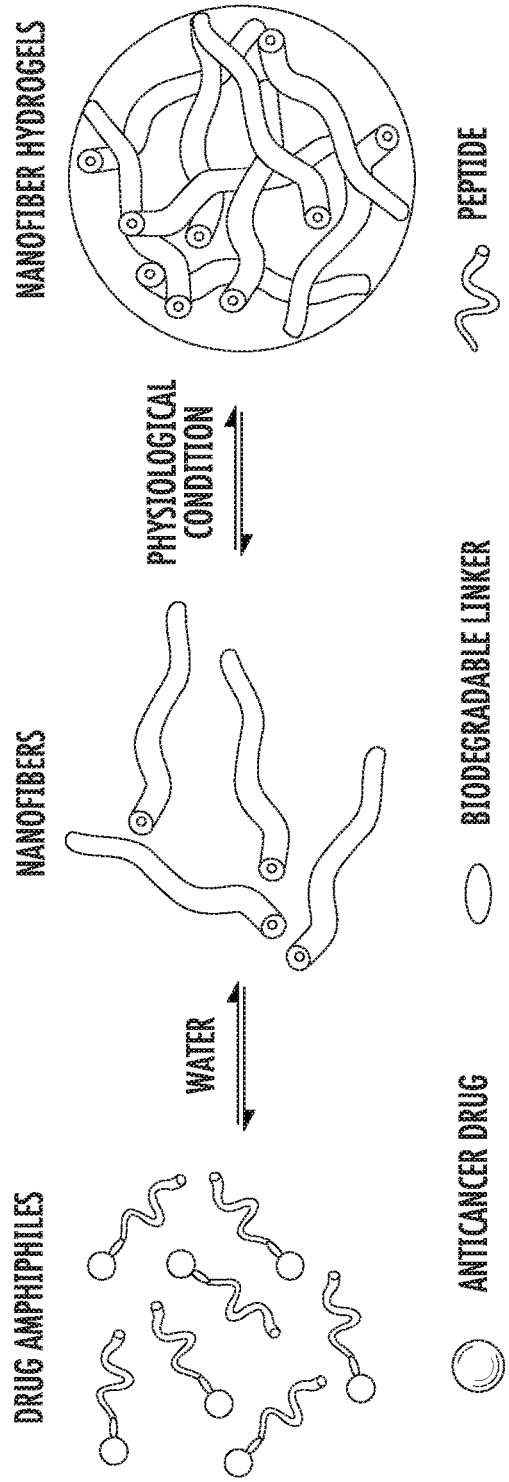
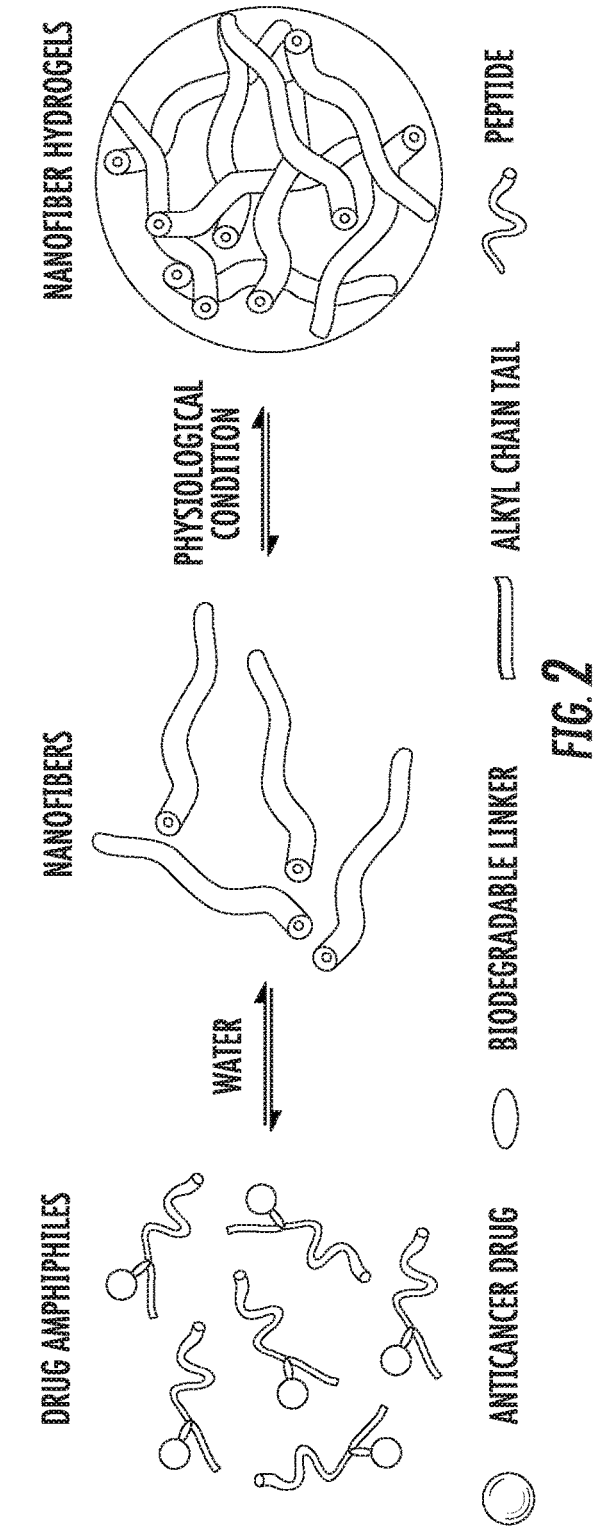

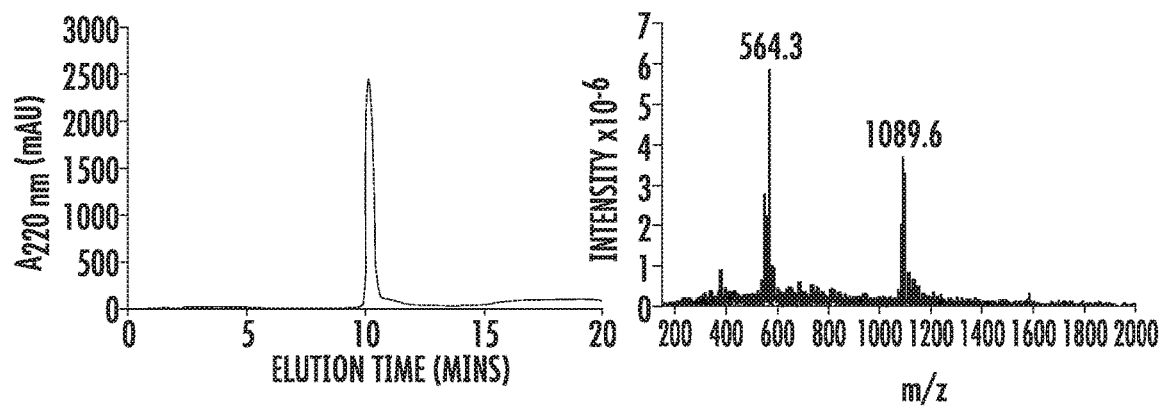
FIG. 4A
FIG. 4B
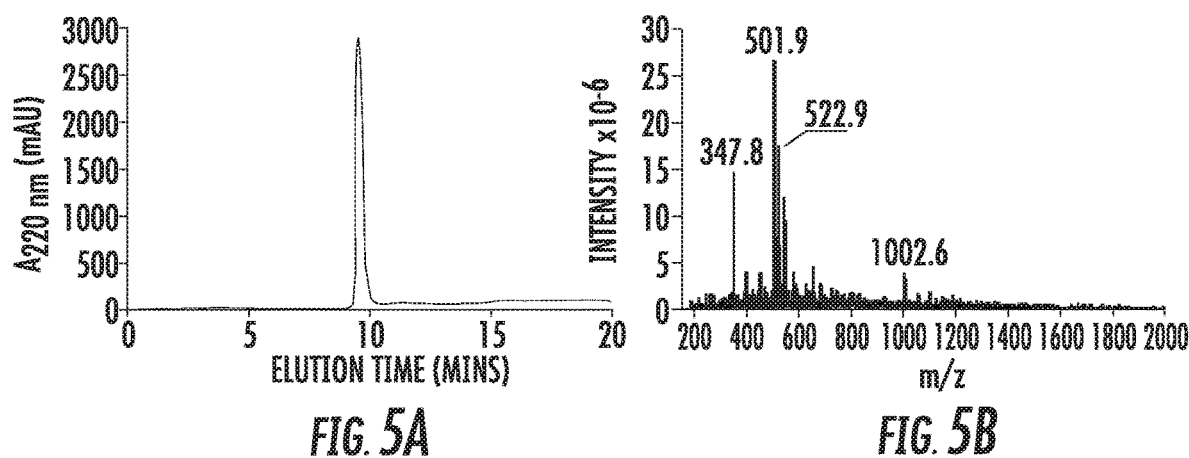
FIG. 5A
FIG. 5B

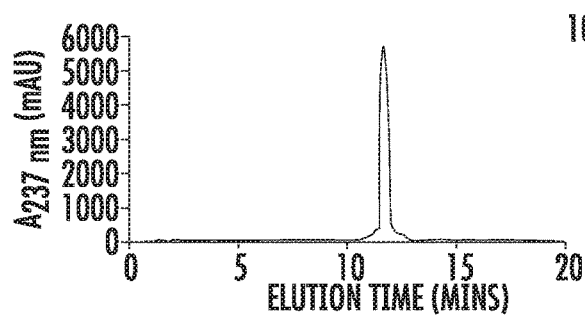 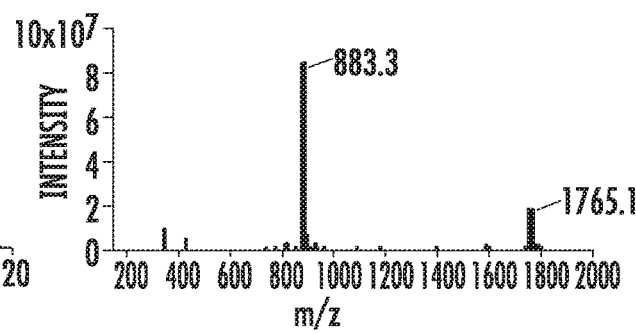
FIG. 7A  FIG. 7B
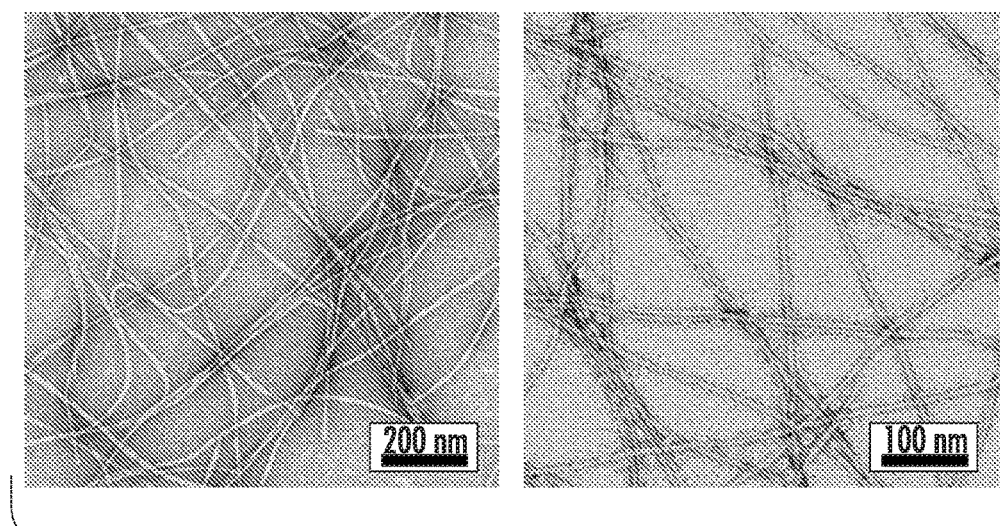
FIG. 8

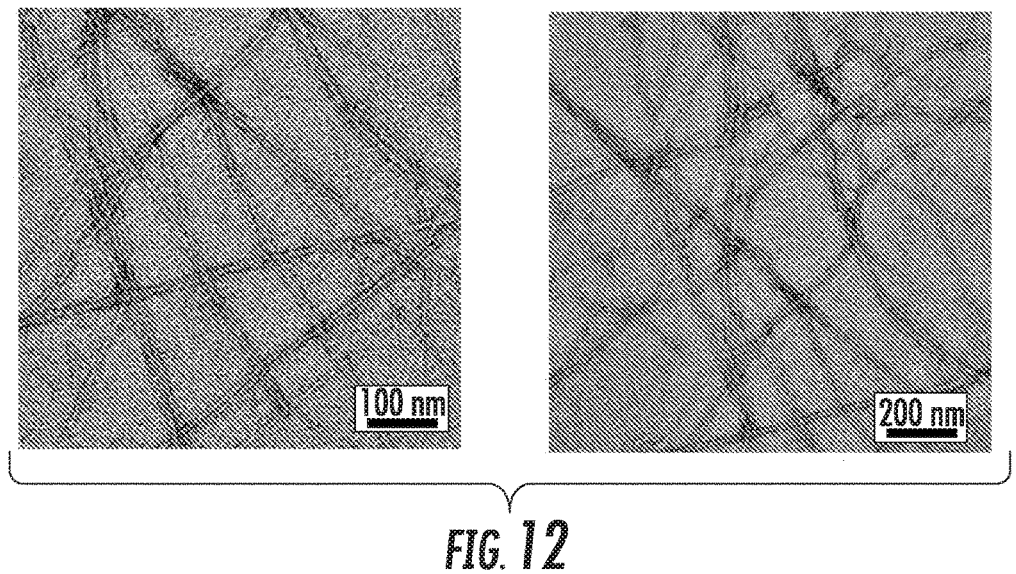
FIG. 12
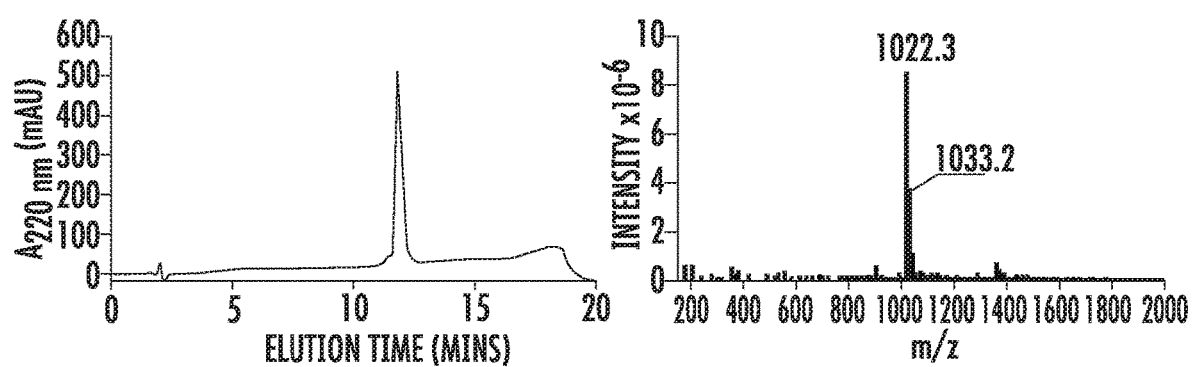
FIG. 13A
FIG. 13B

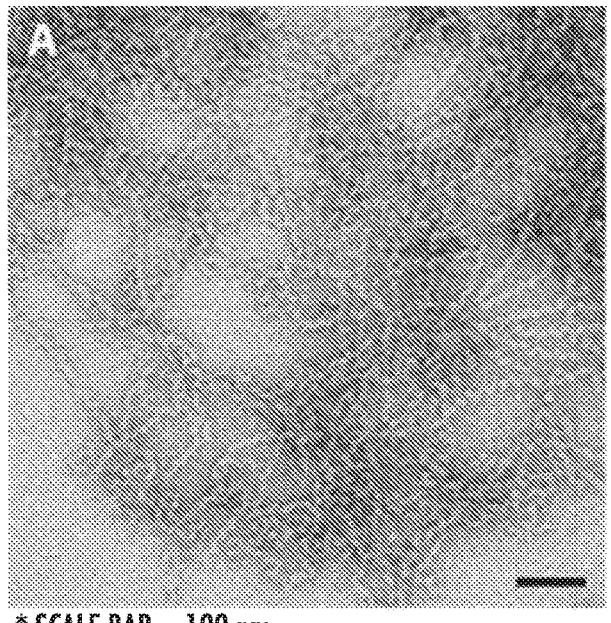
*SCALE BAR = 100 nm
FIG. 14A
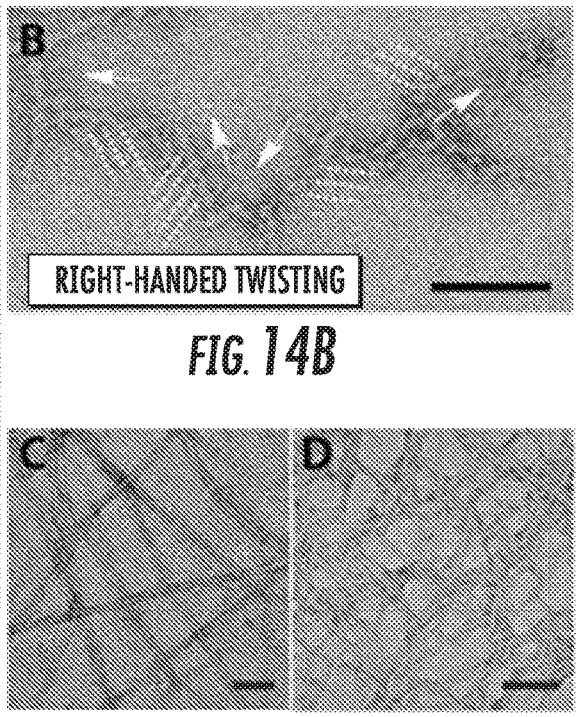
RIGHT-HANDED TWISTING
FIG. 14B
FIG. 14C    FIG. 14D
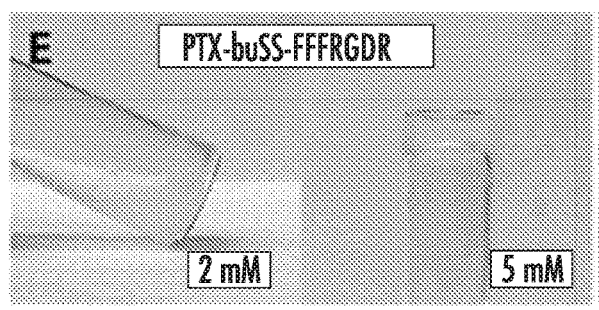
PTX-buSS-FFFRGDR
2 mM    5 mM
FIG. 14E
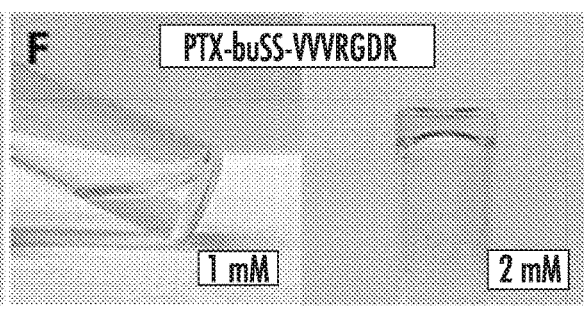
PTX-buSS-VVVRGDR
1 mM    2 mM
FIG. 14F

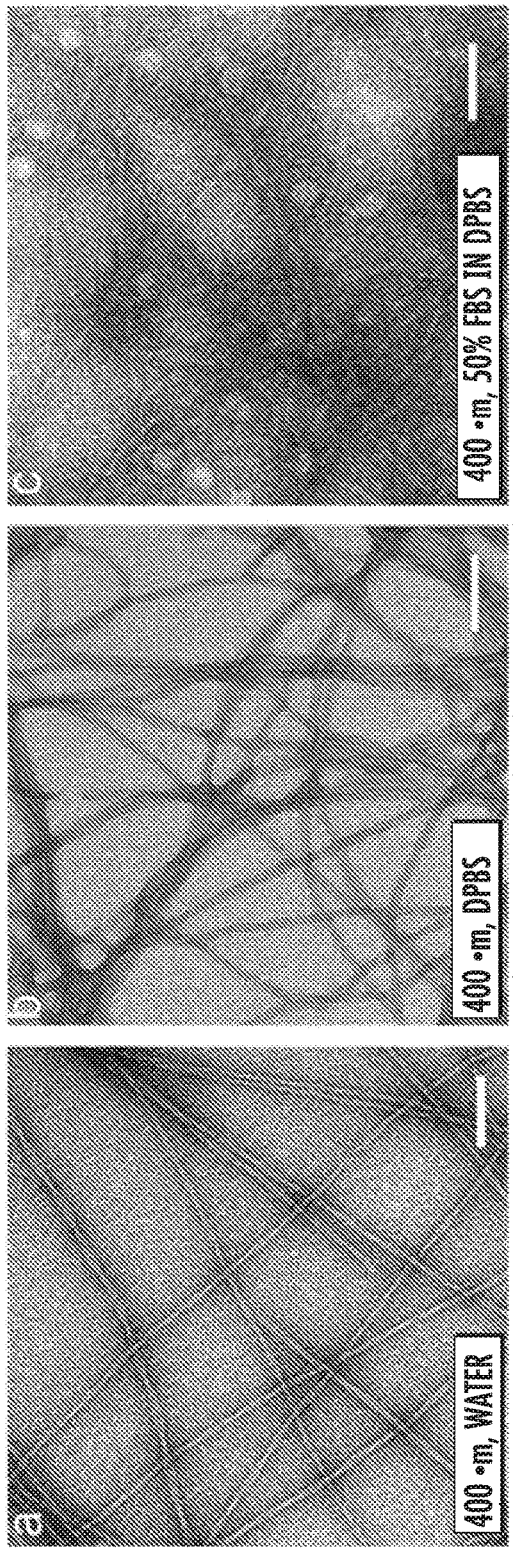
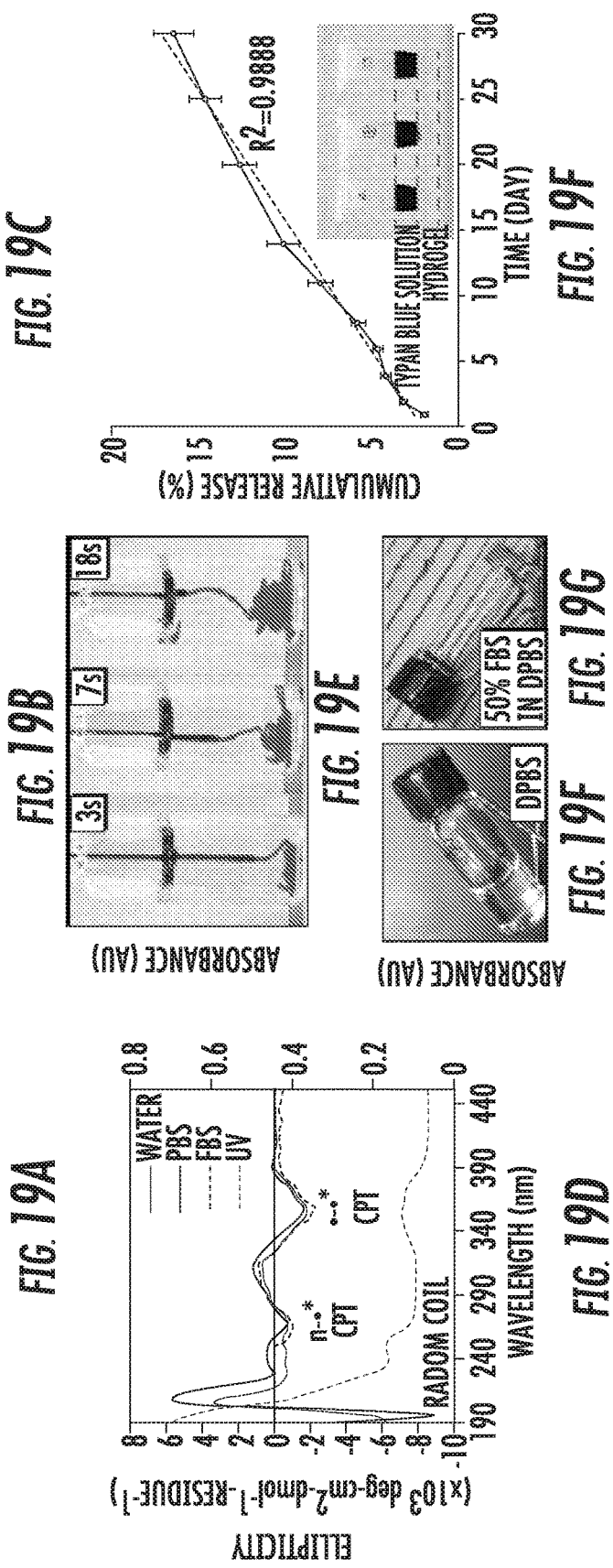

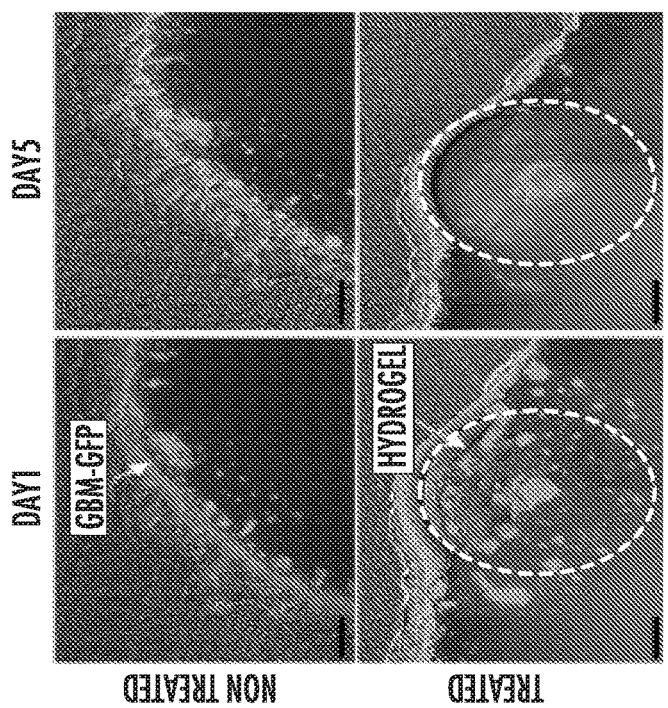
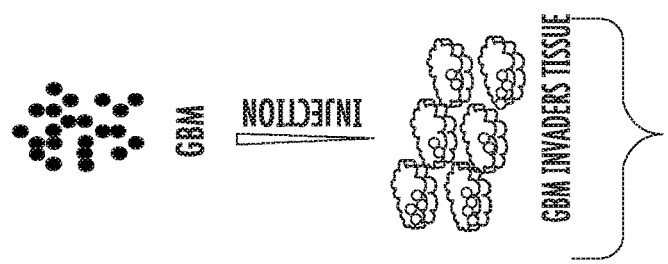
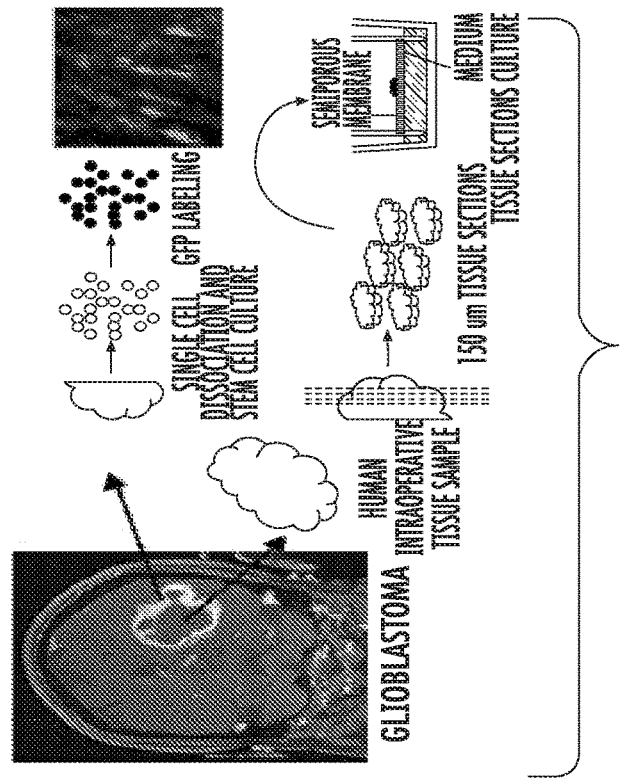
FIG. 20C
FIG. 20B
FIG. 20A

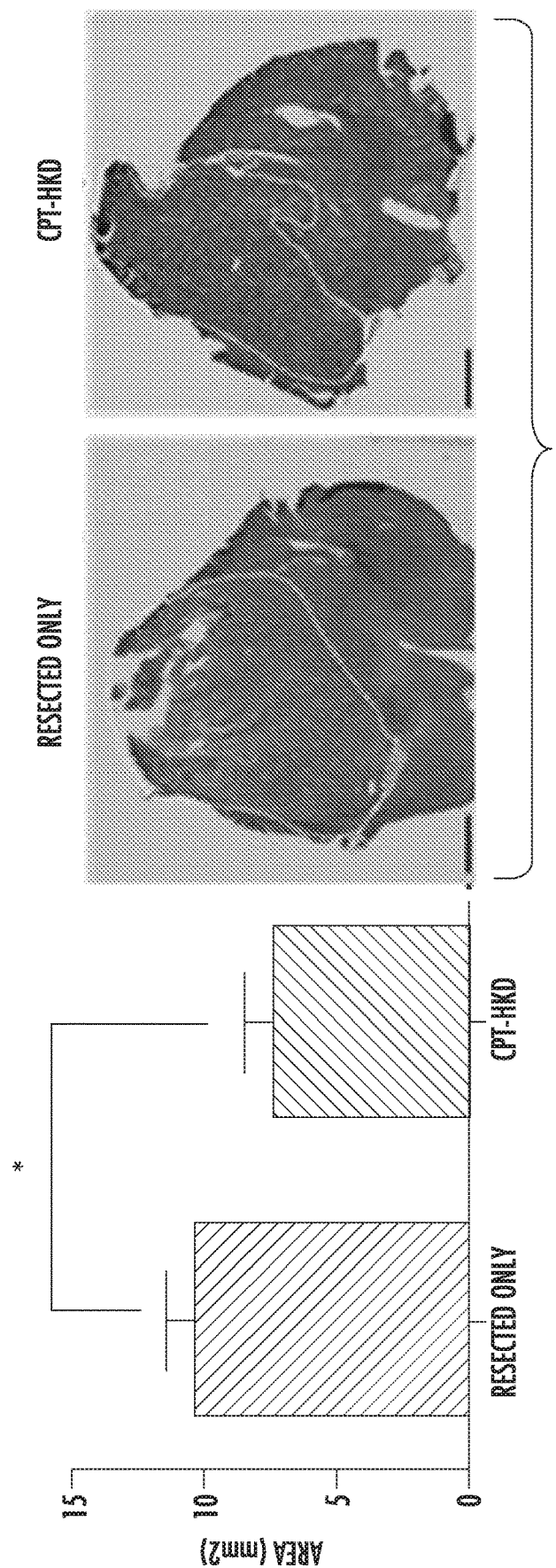

SEQUENCE LISTING

```
<160> NUMBER OF SEQ ID NOS: 8

<210> SEQ ID NO 1
<211> LENGTH: 7
<212> TYPE: PRT
<213> ORGANISM: Artificial Sequence
<220> FEATURE:
<223> OTHER INFORMATION: synthetic sequence

<400> SEQUENCE: 1

Phe Phe Phe Arg Gly Asp Arg
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic sequence

<400> SEQUENCE: 2

Val Val Val Arg Gly Asp Arg
1               5

<210> SEQ ID NO 3
<211> LENGTH: 4
<212> TYPE: PRT
<213> ORGANISM: Artificial Sequence
<220> FEATURE:
<223> OTHER INFORMATION: synthetic sequence

<400> SEQUENCE: 3

Arg Gly Asp Arg
1
```

```
<210> SEQ ID NO 4
<211> LENGTH: 8
<212> TYPE: PRT
<213> ORGANISM: Artificial Sequence
<220> FEATURE:
<223> OTHER INFORMATION: synthetic sequence

<400> SEQUENCE: 4

Lys Phe Phe Phe Arg Gly Asp Arg
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic sequence

<400> SEQUENCE: 5

Cys Val Val Val Arg Gly Asp Arg
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic sequence

<400> SEQUENCE: 6

Cys Phe Phe Phe Arg Gly Asp Arg
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic sequence

<400> SEQUENCE: 7

Gly Val Val Gln Gln His Lys Asp
1               5

<210> SEQ ID NO 8
<211> LENGTH: 5
<212> TYPE: PRT
<213> ORGANISM: Artificial sequence
<220> FEATURE:
<223> OTHER INFORMATION: synthetic sequence

<400> SEQUENCE: 8

Gly Val Val Gln Gln
1               5
```

THERAPEUTIC NANOFIBER HYDROGELS FOR LOCAL TREATMENT OF BRAIN-RELATED DISEASES

CROSS-REFERENCE TO RELATED APPLICATIONS

This application is a 35 U.S.C. § 371 U.S. national entry of International Application PCT/US2016/037781, having an international filing date of Jun. 16, 2016, which claims the benefit of U.S. Provisional Application No. 62/180,264, filed Jun. 16, 2015, the content of each of the aforementioned applications is herein incorporated by reference in their entirety.

STATEMENT OF GOVERNMENTAL INTEREST

This invention was made with government support under grant no. DMR1255281, awarded by the National Science Foundation and grant no. R01NS070024, awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jun. 17, 2021, is named 39010-252_ST25.txt and is 1,693 bytes in size.

BACKGROUND OF THE INVENTION

Malignant gliomas, including the most common type glioblastoma (GBM), are histologically heterogeneous and invasive tumors known as the most devastating neoplasms with high morbidity and mortality. About 24,000 new cases of adult primary malignant gliomas are expected to be diagnosed in the United States in 2015, and an additional 3,000 pediatric gliomas. Despite multimodal treatment including surgery, radiotherapy, and chemotherapy, the disease recurs and is fatal. The overall survival of patients with newly diagnosed GBM is 42.4% at 6 months, 17.7% at 1 year, and only 3.3% at 2 years. Aside from poor survival, deficits in cognitive development have also been described thoroughly among children treated with radiation and systemic chemotherapy for brain tumors. Given its public health importance, there is an unmet need for new treatment strategies to prolong patients' survival while minimizing the side effects, and also improving the quality of life for patients with malignant gliomas. The unique anatomical, physiological and pathological feature of gliomas greatly limits the effectiveness of conventional radiotherapy and chemotherapy. The blood-brain barrier (BBB), a physiological barrier that protects the brain from toxic chemicals, presents the major obstacle for entrance of many therapeutically active compounds and nanoparticle-based drug delivery systems into brain. Systemic chemotherapy with paclitaxel (PTX) and other drugs did not show meaningful clinical benefit with regard to the survival of patients. In addition, the high level of P-glycoproteins in the BBB has also been reported to inhibit the brain penetration and pharmacological activities of many drugs. For this reason, most clinical trials and practices have been focusing on the use of BBB penetrable chemotherapeutics which are mainly alkylating agents that kill cells by attaching an alkyl group to DNA. Another characteristic feature of malignant gliomas is their ability to infiltrate and invade into neighboring tissues. Such local invasion remains an important cause of mortality, and presents a great challenge for current clinical treatments such as surgical intervention.

For most malignant gliomas, maximal surgical resection is usually performed whenever possible. Advances such as MRI-guided neuronavigation, intraoperative MRI, functional MRI, intraoperative mapping, and fluorescence-guided surgery have improved the safety of surgery and increased the extent of resection that can be achieved. However, malignant gliomas cannot be completely eliminated surgically because of their infiltrative nature. After standard radiotherapy, 90% of the tumors recur at the original site, and no significant benefit in survival was observed with increased dosages. Systemic chemotherapy, as adjuvant therapies, prolongs the survival of glioma patients by a couple of months. The survival rate at 2 years among the patients who received radiotherapy and temozolomide (TMZ) was greater than the rate among the patients who received radiotherapy alone (26.5% vs. 10.4%). However, due to the systemic exposure, TMZ dosage is limited by the hematological toxicity, specifically thrombocytopenia and neutropenia.

Malignant gliomas recur in the vicinity of the resection cavity, therefore local chemotherapy that can bypass the BBB and avoid systemic exposure presents a promising strategy. For example, local application of the Gliadel® wafer, a carmustine-loaded polymer implant, as an adjunct to surgery and radiation therapy has been proven to extend the survival of patients with malignant gliomas, strongly suggesting that the combined use of surgical resection and local drug delivery offers an effective treatment strategy to extend the survival of brain tumor patients. However, the encapsulated drug carmustine releases completely from the wafer in about one week. The wafer technology also suffers from poor tissue penetration (the drug concentration drops sharply within a few millimeters) due to capillary loss and metabolism of the drug. These issues are believed to have limited the benefits of Gliadel® wafers, which only extend the median survival of treated patients by a few months.

Thus, there still exists an unmet need for new strategies for treating cancers such as malignant gliomas, which can provide easy implantation at the time of surgery, sustained drug release, high tissue penetration, low morbidity, and introduce effective mechanisms to overcome multidrug resistance, and improved outcome/survival for brain tumor patients.

SUMMARY OF THE INVENTION

The present invention provides herein the design of new monodisperse, amphiphilic prodrugs—that can spontaneously associate into discrete, stable hydrogels with supramolecular nanostructures. These nanofiber hydrogels follow similar principles as those first developed in International Patent Publication No. WO 2014/066002, and incorporated by reference herein. The very nature of the molecular design ensures that a fixed and tunable drug loading can be achieved, without the use of any additional carriers or matrices. The use of these nanofiber hydrogels for local treatment of brain-associated diseases and conditions, including, for example, brain cancer, such as glioblastomas, is also provided herein.

In order to imbue these properties upon a drug or biologically active agent for brain-related diseases, a peptide or oligopeptide with overall hydrophilicity (Pep) is biodegradably linked with the drug or biologically active agent. The peptide or oligopeptide chosen increases the aqueous solubility of the drug or biologically active agent and can promote the formation of well-defined one-dimensional nanostructure architectures including, but not limited to, cylindrical micelles, hollow nanotubes, filaments, fibrils, twisted ribbons, helical ribbons, nanobelts, nanofibers, through preferred secondary structure formation, e.g. beta sheet, alpha helix, poly proline type-II helix, and beta turns. In some embodiments, the nanofiber hydrogels of the present invention are capable of forming three dimensional nanofiber networks and hydrogels in aqueous conditions.

The nanofiber hydrogels of the present invention can provide a sustained release local drug delivery system.

In accordance with an embodiment, the present invention provides a nanofiber hydrogel composition comprising 1 to 4 drug or biologically active agent moieties (D) for brain diseases conjugated to a hydrophilic peptide composition (Pep).

In some embodiments, Pep is a peptide composition having the amino acid sequence $B_n(T)_z$, wherein $B_n$ is an amino acid, of n=0 to 12 amino acids, which can be the same or different, and T is a peptide of z=1 to 15 peptides, with biologically relevant properties including, but not limited to, tumor targeting, tissue penetrating, cell penetrating, apoptotic) or capable of binding to known cellular epitopes, such as integrins or cancer cell receptors.

In accordance with one or more embodiments, D can be conjugated to Pep (D-Pep) through the use of a chemical linker (L) in the form D-L-Pep. L is 0 to 4 biodegradable linkers. The linker can be an ester bond, amide bond, carbonate bond, hydrozone, disulfide bond, or any amino acid with a side chain having a free amino, carboxyl or thiol group, or a short peptide that can be specifically cleaved by a particular enzyme or proteinase.

In accordance with another embodiment, D can be conjugated to Pep (D-Pep) where Pep is linked to a hydrophobic moiety (H). The hydrophobic moiety can be, in some embodiments, an alkyl chain (D-H-Pep).

In accordance with an embodiment, the present invention provides a method of local administration of one or more biologically active agents to a subject comprising in situ application of a composition comprising D-Pep and/or D-L-Pep and/or D-H-Pep to the site of interest within brain.

In accordance with an embodiment, the present invention provides a method of local administration of one or more biologically active agents to a subject comprising in situ injection of a composition comprising a mixture comprising D-Pep and/or D-L-Pep and/or D-H-Pep, and upon contact with body fluids the composition is capable of undergoing a change from solution state to nanofiber gelation state.

In accordance with an embodiment, the delivered nanofiber hydrogels can sustainably release the encapsulated bioactive agents over a long period of time.

In accordance with an embodiment, the released bioactive agent can exert effective in vitro efficacy in killing a number of brain cancer cell lines and primary cells derived from human patients.

In accordance with an embodiment, the nanofiber hydrogels contain a fixed loading of the biological agents which is tunable and precisely defined by the molecular design, and will not require additional matrices/hydrogels for the delivery of the biological agents.

In accordance with an embodiment, the nanofiber form enables diffusion across larger areas relative to individual molecules and avoids capillary loss.

In accordance with an embodiment, the chemical conjugation of biological agents to a short peptide offers an efficient strategy to overcome the Multidrug resistance (MDR) mechanisms that glioma cells possess or may develop over the course of the treatment.

BRIEF DESCRIPTION OF THE DRAWINGS

FIG. 1 illustrates an embodiment of the present invention D-Pep, wherein the self-assembly of amphiphilic monomers into nanofiber hydrogels is depicted. These nanofiber structures enmesh to form hydrogels under certain physiological conditions. The low viscosity of the monomer and nanofiber states offers great flexibility in handling, processing, and delivery.

FIG. 2 depicts a further embodiment of the present invention. In this embodiment, in addition to a biologically active agent or drug for brain-associated diseases, an extra hydrophobic segment (H) is also chemically conjugated to Pep to create a D-H-Pep molecule to form an amphiphilic molecular building molecule with enhanced self-assembly properties in aqueous solution that can lead to formation nanofiber hydrogels.

FIGS. 4A-4B show graphs depicting RP-HPLC trace (A) and MALDI-TOF MS (B) profile of peptide AcCFFFRGDR-OH (SEQ ID NO: 6) showing high purify and the expected molecular mass.

FIGS. 5A-5B show graphs depicting RP-HPLC trace (A) and MALDI-TOF MS (B) profile of peptide AcCVVVRGDR-OH (SEQ ID NO: 5) showing high purify and the expected molecular mass.

FIGS. 7A-7B show graphs depicting RP-HPLC trace (A) and ESI MS (B) profile of an embodiment of the present invention where D is two bumetanide molecules conjugated to Pep (FFFRGDR) (SEQ ID NO:1) as diBum-FFFRGDR (SEQ ID NO: 1). The graphs show high purity and the expected molecular mass.

FIG. 8 is a pair of TEM image where diBum-FFFRGDR (SEQ ID NO: 1) was dissolved in DI water at 5 mM. After 24 aging, PBS buffer was added to trigger hydrogel formation.

FIG. 12 is a pair of TEM images where PTX-VVVRGDR (SEQ ID NO: 2) was dissolved in DI water at 5 mM. After 24 aging, hydrogels were formed. Long fibrous structures were observed in TEM images.

FIGS. 13A-13B show graphs depicting RP-HPLC trace (A) and ESI MS (B) profile of PTX-FFFRGDR (SEQ ID NO: 1) showing high purify and the expected molecular mass.

FIGS. 14A-14F depict representative TEM images of PTX-buSS-FFFRGDR (SEQ ID NO: 1) (A and B), PTX-buSS-VVVRGDR (SEQ ID NO: 2) (C) and C16-FFFRGDR (SEQ ID NO: 1) (D). PTX-buSS-FFFRGDR (SEQ ID NO: 1) self-assembled into "super coil" nanofibers with right-handed twisting, while two control molecules formed straight fibers. Determination of critical gelation concentration of PTX-buSS-FFFRGDR (SEQ ID NO: 1) (E) and PTX-buSS-VVVRGDR (SEQ ID NO: 2) (F): viscous liquids at the concentration of 2 mM and 1 mM, respectively; and self-supported hydrogels at the concentration of 5 mM and 2 mM, respectively.

FIGS. 19A-19F depict the filamentous nanostructures formed by the new CPT-HKD molecule under various conditions, as well as their gelation properties.

FIGS. 20A-20C show the tissue organotypic-GBM invasion model directly obtained from the Operating Room. (A) Tumor tissue from GBM patients is collected in the OR, from which single primary-derived cells are obtained and labeled with GFP. Tumor tissue can also be sliced in 150-300 µm slices and kept alive for 2 weeks in a semiporous membrane fed with media from the bottom (organotypic tissue). (B) GBM-GFP tagged cells can be injected on the surface of the organotypic slices (1×10$^5$ cells) and invade the tissue slices. 24 h after invasion of the GBMs 4 µl of CPT-HKD hydrogel are placed on top of the tissue. (C) Representative images of the organotypic slices showing GBM-GFP cells invading the tissue (n=3). (scale bar 500 µm).

FIGS. 23A-23B depict CPT nanofiber hydrogels treatment reduces brain tumor area. A) Tumor area of CPT gel compared versus resection only group after 1 month of treatment. Tumor area was determined by stereological analysis of consecutive 10 µm thick sections. p value was calculated by Mann-Whitney U (p=0.037). B) H&E image examples from resection only and CPT treated mice. Scale bar: 1 mm.

DETAILED DESCRIPTION OF THE INVENTION

Figure 3:
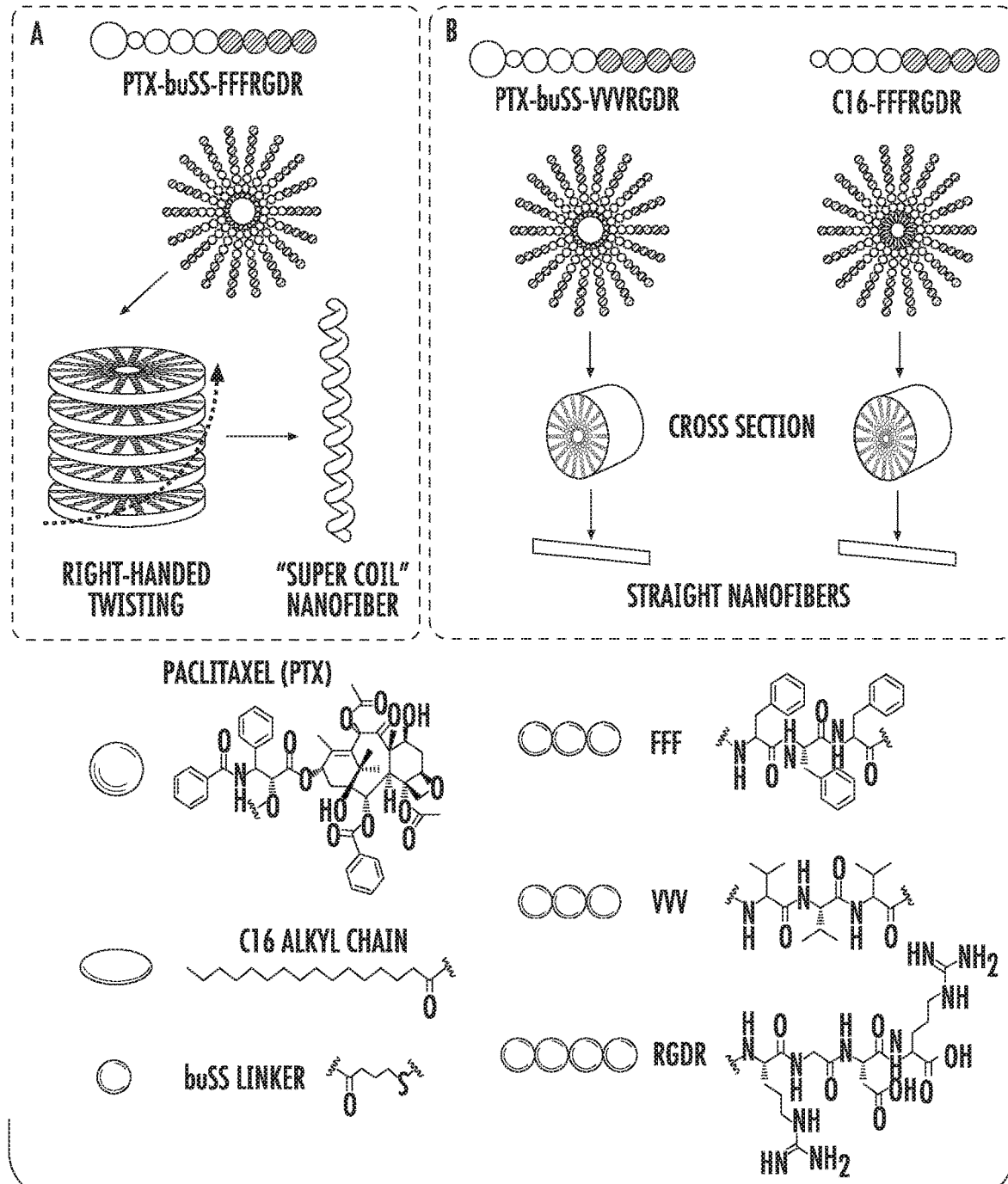
FIGS. 3A-3B are schematic illustrations of the designed PTX-buSS-FFFRGDR (SEQ ID NO: 1) DA (A) and two control molecules PTX-buSS-VVVRGDR (SEQ ID NO: 2) and C16-FFFRGDR (SEQ ID NO: 1) (B). PTX-buSS-FFFRGDR (SEQ ID NO: 1) self-assembled into a right-handed twisted "super coil" nanofibers with high drug loading (42%), while PTX-buSS-VVVRGDR (SEQ ID NO: 2) and C16-FFFRGDR (SEQ ID NO: 1) formed straight nanofibers after substitution of either hydrophobic domain or π-π interaction domain.

The compositions and methods of the present invention demonstrate a strategy to tune active drug compounds release rate by altering the drug amphiphiles molecule's aromaticity and hydrophobicity in "super-coil" nanofilaments. Particularly, the inherent properties of hydrogelators leads to hierarchal differences in nanostructures' morphology and chemotherapeutic efficacies. Hydrogels formed by "supercoil" nanofibers demonstrate stable supramolecular nanostructures and tunable drug release rates. In an embodiment, the anticancer drug gradient release from a PTX-loaded hydrogel molecule of the present invention acts as chemotherapeutic reagent reservoir for local treatment over a long time scale. Accordingly, the compositions and methods of the present invention can be extended to fabricate morphologies and stability of nanostructures with π-π interactions and hydrophobic interactions. These nanofilaments with various structures and mechanical properties will lead to new opportunities for the local treatment and drug delivery for multiple cancer chemotherapies.

In accordance with an embodiment, the present invention provides a nanofiber hydrogel composition comprising 1 to 4 drug or biologically active agent moieties (D) conjugated to a hydrophilic peptide composition (Pep), which provide a sustained release local drug delivery system. The use of such compositions is not limited to local in situ release of one or more biologically active agents into the tissues in contact with the nanofiber hydrogel composition.

It will be understood by those of ordinary skill in the art, that in some embodiments, D can represent two or more different hydrophobic drug molecules. For example, D can include a first drug (D1) and second drug (D2) which can be, for example, chemotherapeutic agents which are not the same. In other embodiments, D can represent three or four different drug molecules (D1, D2, D3, D4) each linked by a biodegradable linker, which can be the same or different, to a PEP portion of the molecule of the present invention.

Without being limited to any particular example, the pharmaceutical composition of the present invention can be a hetero-dual drug amphiphile comprising a first drug molecule of a first drug and a second drug linked by the same or different linker, for example buSS, to the PEP portion.

It is contemplated that the nanofiber hydrogels of the present invention can be made in solid, or liquid form, and then applied to the tissues of interest by spraying, injection, or otherwise applying the compositions directly to the tissues.

In some preferred embodiments, the compositions of the present invention are prepared as a dry powder and then come in contact with aqueous solutions, for example, such as physiological buffers or tissue fluids such as blood or lymph, and will spontaneously form aqueous nanofiber hydrogels. In alternative embodiments, the compositions of the present invention can be formulated in a viscous liquid or vitrigel form and then are applied to the tissues of interest to become aqueous nanofiber hydrogels.

In some embodiments, the biologically active agent or drug (D) acts as the hydrophobic portion of molecule in the nanofiber hydrogel compositions of the present invention.

It is contemplated that the other hydrophobic molecules can be used in the D-Pep molecules of the present invention. For example, other hydrophobic molecules such as steroids, other conjugated ring containing molecules, and hydrophobic drugs can be used.

As used herein, the term "hydrophobic" biologically active agents or drug molecules describes a heterogeneous group of molecules that exhibit poor solubility in water but that are typically, but certainly not always, soluble in various organic solvents. Often, the terms slightly soluble (1-10 mg/ml), very slightly soluble (0.1-1 mg/ml), and practically insoluble (<0.1 mg/ml) are used to categorize such substances. Drugs such as steroids and many anticancer drugs are important classes of poorly water-soluble drugs; however, their water solubility varies over at least two orders of magnitudes. Typically, such molecules require secondary solubilizers such as carrier molecules, liposomes, polymers, or macrocyclic molecules such as cyclodextrins to help the hydrophobic drug molecules dissolve in aqueous solutions necessary for drug delivery in vivo. Other types of hydrophobic drugs show even a lower aqueous solubility of only a few ng/ml. Since insufficient solubility commonly accompanies undesired pharmacokinetic properties, the high-throughput screening of kinetic and thermodynamic solubility as well as the prediction of solubility is of major importance in discovery (lead identification and optimization) and development.

In some embodiments, a hydrophobic moiety can be linked to Pep and to a drug (D). Examples of hydrophobic moieties that can be used in accordance with the present invention include long chain fatty acids, such a stearate, and/or palmitate.

In some embodiments, Pep is a peptide composition having the amino acid sequence $B_n(T)_z$, wherein $B_n$ is an amino acid, of n=0 to 12 amino acids, which can be the same or different, and T is a peptide of z=1 to 15 amino acids, with biologically relevant properties including, but not limited to, tumor targeting, tissue penetrating, cell penetrating, apoptotic) or capable of binding to known cellular epitopes, such as integrins or cancer cell receptors, and derivatives, or functional fragments or functional homolog of such peptides.

The term, "amino acid" includes the residues of the natural α-amino acids (e.g., Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and non-natural amino acids. Many types of amino acid residues are useful in the polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

Reference herein to "derivatives" includes parts, fragments and portions of the Pep portion of the molecule. A derivative also includes a single or multiple amino acid substitution, deletion and/or addition. Homologues include functionally, structurally or stereochemically similar peptides from the naturally occurring peptide or protein. All such homologs are contemplated by the present invention.

Analogs and mimetics include molecules which include molecules which contain non-naturally occurring amino acids or which do not contain amino acids but nevertheless behave functionally the same as the peptide. Natural product screening is one useful strategy for identifying analogs and mimetics.

Examples of incorporating non-natural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A partial list of known non-natural amino acid contemplated herein is shown in Table 1.

TABLE 1

Non-natural Amino Acids

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine |  | Chexa L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |

TABLE 1-continued

Non-natural Amino Acids

| Non-conventional amino acid | Code | Non-conventional amino acid | Code |
|---|---|---|---|
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenylethylamino)cyclopropane | Nmbc | | |

Analogs of the subject peptides contemplated herein include modifications to side chains, incorporation of non-natural amino acids and/or their derivatives during peptide synthesis and the use of crosslinkers and other methods which impose conformational constraints on the peptide molecule or their analogs.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers can be used, for example, to stabilise 3D conformations, using homo-bifunctional crosslinkers such as the bifunctional imido esters having (CH$_2$)$_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of C$_α$ and N$_α$-methylamino acids, introduction of double bonds between C$_α$ and C$_β$ atoms of amino acids and the formation of cyclic peptides or analogues by introducing covalent bonds such as forming an amide bond between the N and C termini, between two side chains or between a side chain and the N or C terminus.

The present invention further contemplates small chemical analogs of the naturally occurring Pep moiety. Chemical analogs may not necessarily be derived from the peptides themselves but may share certain conformational similarities. Alternatively, chemical analogs may be specifically designed to mimic certain physiochemical properties of the peptides. Chemical analogs may be chemically synthesized or may be detected following, for example, natural product screening.

In some embodiments, T can be RGD or RGDR (SEQ ID NO: 3) or HDK or derivatives thereof, having z=1 to 6 repeating moieties.

In accordance with an embodiment of Pep, B is phenylalanine (F) with n=3 and T is RGDR with z=1, such that Pep is FFFRGDR (SEQ ID NO: 1) or when Bn=0 and T=RGDR and z=1, (SEQ ID NO: 3).

Other possible targeting peptides which can be used in conjunction with the compositions of the present invention include tumor associated antigens. Examples of such antigens include CEA, TAG-72, CyclinB1, Ep-CAM, Her2/neu, CDK4, fibronectin, p53, ras, and other.

In accordance with one or more embodiments, D can be conjugated to Pep (D-Pep) through the use of a chemical linker (L) in a form D-L-Pep. L is 0 to 4 biodegradable linkers. The linker can be an ester bond, amide bond, carbonate bond, hydrozone, disulfide bond, or any amino acid with a side chain having a free amino, carboxyl or thiol group, or a short peptide that can be specifically cleaved by a particular enzyme or proteinase. In an embodiment, the linker can be a C$_1$-C$_6$ acyl-disulfide group. For example, the linker can be (4-(pyridin-2-yldisulfanyl)butanoate) (buSS).

The buSS linker has a disulfide moiety that allows it to be reductively cleaved primarily intracellularly by glutathione. In particular, the concentration of glutathione inside tumor cells is 100 to 1000 times higher than in the interstitial fluid, thus allowing the compositions of the present invention to act as a prodrug and enter the cell intact. Once inside the cell, the reduction of the linker bonds by glutathione occurs, and the free hydrophobic drug molecule can act on its target. It will be understood by those of ordinary skill in the art that other linker moieties can be used where they interact with the hydrophilic peptide in a similar manner.

As used herein, the term "biologically active agent" include any compound, biologics for treating brain-related diseases, e.g. drugs, inhibitors, and proteins. An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc.

Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

Specific examples of useful biologically active agents the above categories include: anti-neoplastics such as androgen inhibitors, antimetabolites, cytotoxic agents, and immunomodulators. More specifically, non-limiting examples of useful biologically active agents include the following therapeutic categories antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics, such as carboplatin and cisplatin; carmustine (BCNU); methotrexate; fluorouracil (5-FU) and gemcitabine; goserelin, leuprolide, and tamoxifen, aldesleukin, interleukin-2, docetaxel, etoposide, interferon; paclitaxel, other taxane derivatives, tretinoin (ATRA); bleomycin, dactinomycin, daunorubicin, doxorubicin, and mitomycin; vinblastine and vincristine.

In accordance with some embodiments, the biologically active agents (D) covalently linked to Pep include bumetanide, verteporfin, vorapaxar, camptothecin and paclitaxel.

In accordance with another embodiment, the present invention provides a D-Pep composition having the following formula:

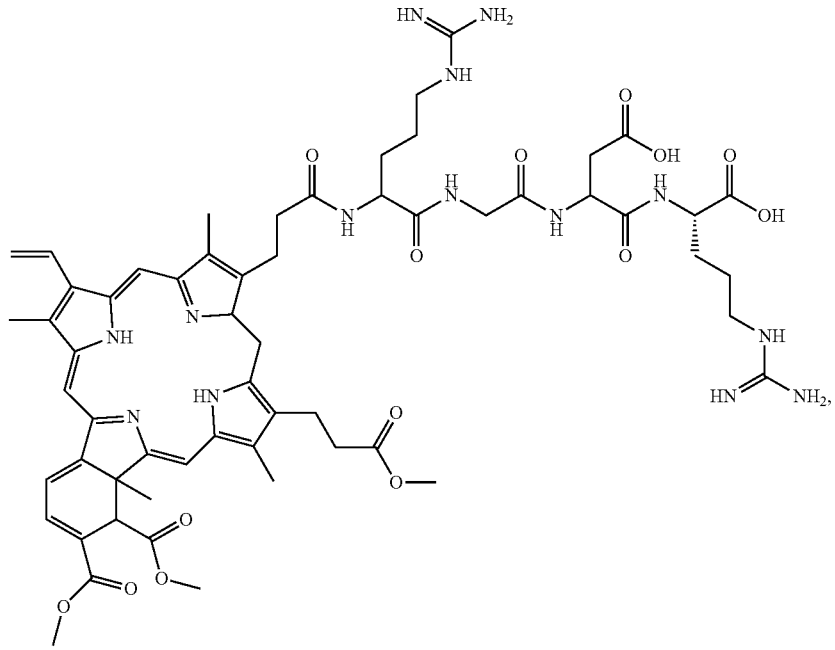

wherein D is the drug verteporfin, L is 0, Pep is $(B)_0$ and T is (RGDR) (SEQ ID NO: 3) with z=1, and wherein the verteporfin molecule is covalently linked via a lysine amino acid linker.

In accordance with a further embodiment, the present invention provides a D-Pep composition having the following formula:

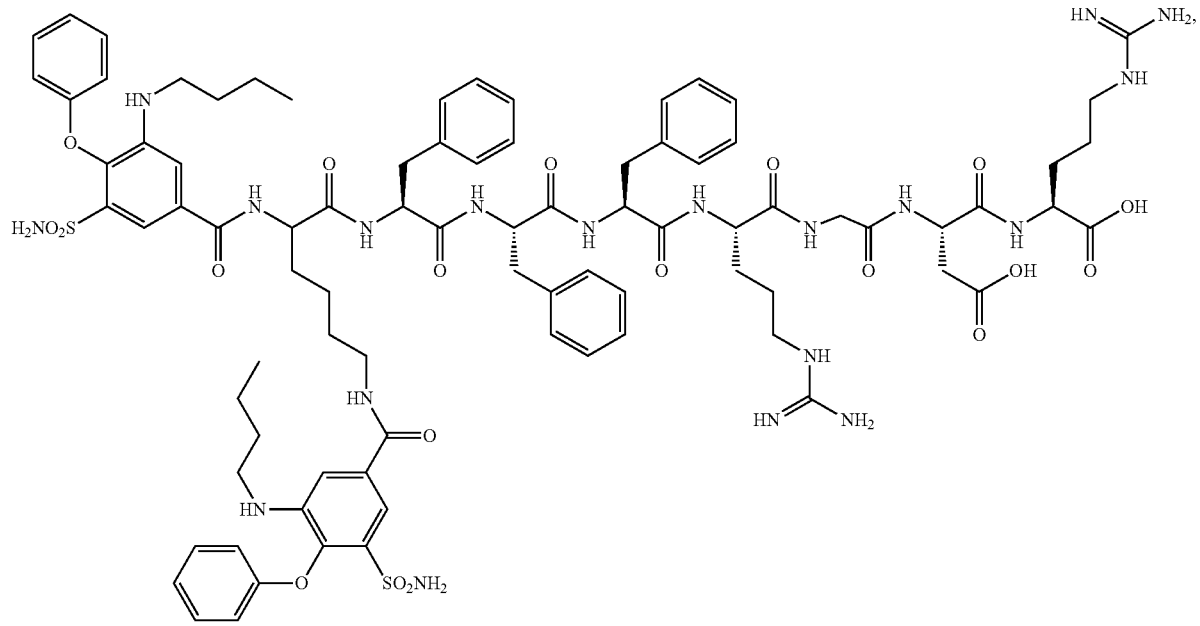

wherein D=2 bumetanide molecules, L is 0, Pep is (FFF) and T is (RGDR) (SEQ ID NO: 3) with z=3, and wherein the two bumetanide molecules are covalently linked via a lysine amino acid linker.

In accordance with a further embodiment, the present invention provides a D-Pep composition having the following formula:

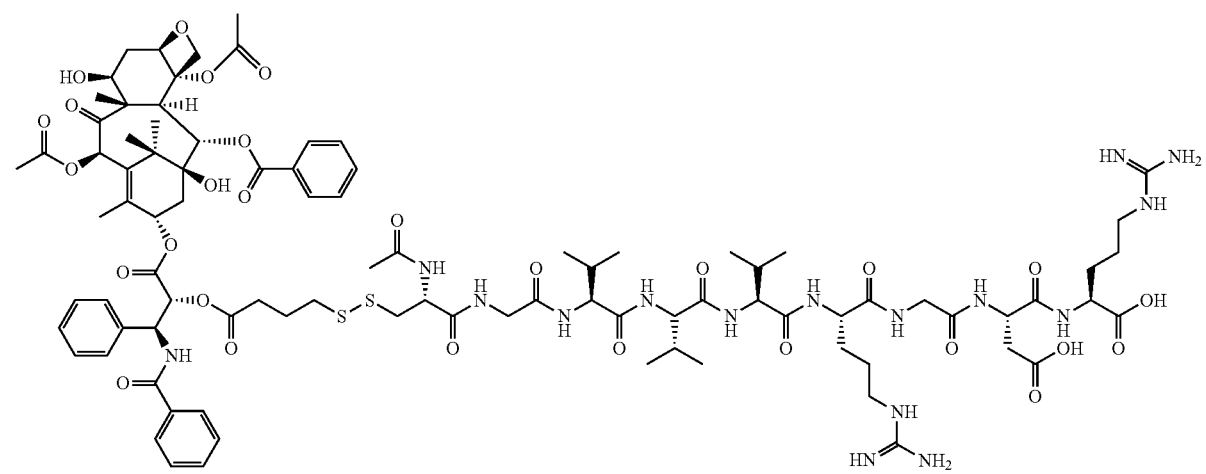

wherein D=1 paclitaxel molecule, L is 1 (disulfanylbutanoate) (buSS) linker, Pep is (VVV) and T is (RGDR) (SEQ ID NO: 3) with z=3, and wherein the one paclitaxel molecule is covalently linked via a disulfide linker.

In accordance with yet another embodiment, the present invention provides a D-Pep composition having the following formula:

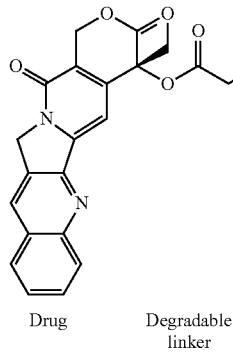 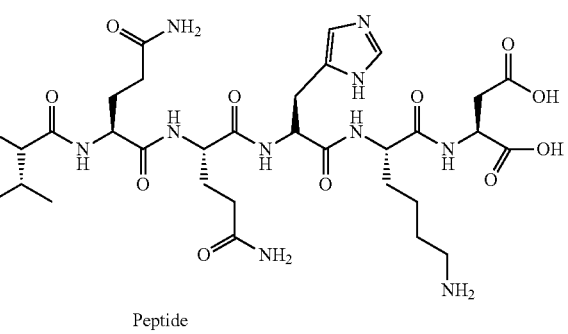

Drug    Degradable
        linker                                              Peptide wherein D=1 camptothecin molecule, L is 1 (disulfanylbutanoate) (buSS) linker, Pep is (GVVQQ) (SEQ ID NO: 8) and T is (HKD) with z=4, and wherein the one paclitaxel molecule is covalently linked via a disulfide linker.

As used herein, the term "biologically active agent" can also include imaging agents for use in identifying the location of the molecules in the tissues. In accordance with an embodiment, the imaging agent is a fluorescent dye. The dyes may be emitters in the visible or near-infrared (NIR) spectrum. Known dyes useful in the present invention include carbocyanine, indocarbocyanine, oxacarbocyanine, thüicarbocyanine and merocyanine, polymethine, coumarine, rhodamine, xanthene, fluorescein, boron-dipyrromethane (BODIPY), Cy5, Cy5.5, Cy7, VivoTag-680, VivoTag-5680, VivoTag-5750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

Organic dyes which are active in the NIR region are known in biomedical applications. However, there are only a few NIR dyes that are readily available due to the limitations of conventional dyes, such as poor hydrophilicity and photostability, low quantum yield, insufficient stability and low detection sensitivity in biological system, etc. Significant progress has been made on the recent development of NIR dyes (including cyanine dyes, squaraine, phthalocyanines, porphyrin derivatives and BODIPY (borondipyrromethane) analogues) with much improved chemical and photostability, high fluorescence intensity and long fluorescent life. Examples of NIR dyes include cyanine dyes (also called as polymethine cyanine dyes) are small organic molecules with two aromatic nitrogen-containing heterocycles linked by a polymethine bridge and include Cy5, Cy5.5, Cy7 and their derivatives. Squaraines (often called Squarylium dyes) consist of an oxocyclobutenolate core with aromatic or heterocyclic components at both ends of the molecules, an example is KSQ-4-H. Phthalocyanines, are two-dimensional 18π-electron aromatic porphyrin derivatives, consisting of four bridged pyrrole subunits linked together through nitrogen atoms. BODIPY (boron-dipyrromethane) dyes have a general structure of 4,4'-difluoro-4-bora-3a, 4a-diaza-s-indacene) and sharp fluorescence with high quantum yield and excellent thermal and photochemical stability.

Other imaging agents which are attached to the nanofiber hydrogel compositions of the present invention include PET and SPECT imaging agents. The most widely used agents include branched chelating agents such as di-ethylene triamine penta-acetic acid (DTPA), 1,4,7,10-tetra-azacyclododecane-1,4,7,10-tetraacetic acid (DOTA) and their analogs. Chelating agents, such as di-amine dithiols, activated mercaptoacetyl-glycyl-glycyl-gylcine (MAG3), and hydrazidonicotinamide (HYNIC), are able to chelate metals like $^{99m}$Tc and $^{186}$Re. Instead of using chelating agents, a prosthetic group such as N-succinimidyl-4-$^{18}$F-fluorobenzoate ($^{18}$F-SFB) is necessary for labeling peptides with $^{18}$F. In accordance with a preferred embodiment, the chelating agent is DOTA.

Various forms of the biologically active agents may be used. These include, without limitation, such forms as uncharged molecules, molecular complexes, salts, ethers, esters, amides, prodrug forms and the like, which are biologically activated when implanted, injected or otherwise placed into a subject.

In accordance with one or more embodiments, D can be conjugated to Pep through the use of a chemical linker. The linker can be an ester bond, amide bond, carbonate bond, hydrozone, or any amino acid with a side chain having a free amino, carboxyl or thiol group, or a short peptide that can be specifically cleaved by a particular enzyme or proteinase.

In some embodiments, the linker can be any amino acid with a side chain having a free amino, carboxyl or disulfide group. Exemplary amino acids useful as amino acid linkers in the nanofiber hydrogels of the present invention include lysine (K), glutamic acid (E), arginine (R) and cysteine (C).

It is contemplated that the biologically active agents (D) are covalently linked to the Pep via a biodegradable bond. For example, amino groups, carboxyl groups and disulfide bonds are capable of being cleaved in vitro by various chemical and biological or enzymatic processes.

In certain embodiments, nanofiber hydrogel compositions of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between about 25 and 37° C. In other embodiments, the nanofiber hydrogel degrades in a period of between about one hour and several weeks, depending on the desired application. In some embodiments, the nanofiber hydrogel may include a detectable agent that is released on degradation.

"Gel" refers to a state of matter between liquid and solid, and is generally defined as a cross-linked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (i.e., the shape is discrete enough to maintain three dimensions on a two-dimensional surface).

By "hydrogel" is meant a water-swellable polymeric matrix that can absorb water to form elastic gels, wherein "matrices" are three-dimensional networks of macromolecules held together by covalent or noncovalent crosslinks. On placement in an aqueous environment, dry hydrogels swell by the acquisition of liquid therein to the extent allowed by the degree of cross-linking.

Starting materials and reagents used in preparing these nanofiber hydrogel compositions of the present invention are either available from commercial suppliers such as Aldrich Chemical Company (Milwaukee, Wis.), Bachem (Torrance, Calif.), Sigma (St. Louis, Mo.), or are prepared by methods well known to the person of ordinary skill in the art following procedures described in such references as Fieser and Fieser's Reagents for Organic Synthesis, vols. 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, 4$^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art. For example, N-pyrrolidineacetic acid is described in Dega-Szafran Z and Pryzbylak R. Synthesis, IR, and NMR studies of zwitterionic α-(1-pyrrolidine)alkanocarboxylic acids and their N-methyl derivatives. J. Mol. Struct.: 436-7, 107-121, 1997; and N-piperidineacetic acid is described in Matsuda O, Ito S, and Sekiya M. each article herein expressly incorporated herein fully by reference.

Conveniently, synthetic production of the polypeptides of the invention may be according to the solid-phase synthetic method described by Goodman M. (ed.), "Synthesis of Peptides and Peptidomimetics" in Methods of organic chemistry (Houben-Weyl) (Workbench Edition, E22a, b, c, d, e; 2004; Georg Thieme Verlag, Stuttgart, N.Y.), herein expressly incorporated fully by reference. This technique is well understood and is a common method for preparation of peptides. The general concept of this method depends on attachment of the first amino acid of the chain to a solid polymer by a covalent bond. Succeeding protected amino acids are added, on at a time (stepwise strategy), or in blocks (segment strategy), until the desired sequence is assembled. Finally, the protected peptide is removed from the solid resin support and the protecting groups are cleaved off. By this procedure, reagents and by-products are removed by filtration, thus eliminating the necessity of purifying intermediaries.

Amino acids may be attached to any suitable polymer as a resin. The resin must contain a functional group to which the first protected amino acid can be firmly linked by a covalent bond. Various polymers are suitable for this purpose, such as cellulose, polyvinyl alcohol, polymethylmethacrylate and polystyrene. Suitable resins are commercially available and well known to those of skill in the art. Appropriate protective groups usable in such synthesis include tert-butyloxycarbonyl (BOC), benzyl (Bzl), t-amyloxycarbonyl (Aoc), tosyl (Tos), o-bromo-phenylmethoxycarbonyl (BrZ), 2,6-dichlorobenzyl (BzlCl$_2$), and phenylmethoxycarbonyl (Z or CBZ). Additional protective groups are identified in Goodman, cited above, as well as in McOmie J F W: Protective Groups in Organic Chemistry, Plenum Press, New York, 1973, both references expressly incorporated fully herein by reference.

General procedures for preparing nanofiber hydrogel compositions of the present invention of this invention involve initially attaching a carboxyl-terminal protected amino acid to the resin. After attachment the resin is filtered, washed and the protecting group on the alpha-amino group of the carboxyl-terminal amino acid is removed. The removal of this protecting group must take place, of course, without breaking the bond between that amino acid and the resin. The next amino, and if necessary, side chain protected amino acid, is then coupled to the free amino group of the amino acid on the resin. This coupling takes place by the formation of an amide bond between the free carboxyl group of the second amino acid and the amino group of the first amino acid attached to the resin. This sequence of events is repeated with successive amino acids until all amino acids are attached to the resin. Finally, the protected peptide is cleaved from the resin and the protecting groups removed to reveal the desired peptide. The cleavage techniques used to separate the peptide from the resin and to remove the protecting groups depend upon the selection of resin and protecting groups and are known to those familiar with the art of peptide synthesis.

Peptides may be cyclized by the formation of a disulfide bond between two cysteine residues. Methods for the formation of such bonds are well known and include such methods as those described in G. A. Grant (Ed.) Synthetic Peptides A User's Guide 2$^{nd}$ Ed., Oxford University Press, 2002, W. C. Chan and P. D. White (Eds.) Fmoc Solid Phase Synthesis A Practical Approach, Oxford University Press, 2000 and references therein.

Alternative techniques for peptide synthesis are described in Bodanszky et al, Peptide Synthesis, 2nd ed, John Wiley and Sons, New York, 1976, expressly incorporated herein fully by reference. For example, the peptides of the invention may also be synthesized using standard solution peptide synthesis methodologies, involving either stepwise or block coupling of amino acids or peptide fragments using chemical or enzymatic methods of amide bond formation (see, e.g. H. D. Jakubke in The Peptides, Analysis, Synthesis, Biology, Academic Press, New York, 1987, p. 103-165; J. D. Glass, ibid., pp. 167-184; and European Patent 0324659 A2, describing enzymatic peptide synthesis methods.) These solution synthesis methods are well known in the art.

Commercial peptide synthesizers, such as the Applied Biosystems Model 430A, are available for the practice of these methods.

In one aspect of this invention, various forms of a biologically active agent may be used which are capable of being released by the nanofiber hydrogel composition, for example, into adjacent tissues or fluids upon administration to a subject.

In one embodiment, the repair of damaged tissue may be carried out within the context of any standard surgical process allowing access to and repair of the tissue, including open surgery and laparoscopic techniques. Once the damaged tissue is accessed, a nanofiber hydrogel composition of the invention is placed in contact with the damaged tissue along with any surgically acceptable patch or implant, if needed.

In accordance with yet another embodiment, the present invention provides a method of treating a disease in a subject comprising administering to the mammal a therapeutically effective amount of the compositions described above, sufficient to slow, stop or reverse the disease in the mammal.

In accordance with an embodiment, the present invention provides a method of local administration of one or more biologically active agents to a subject comprising in situ application of a composition comprising D-Pep and/or D-L-Pep to the site of interest.

In accordance with an embodiment, the present invention provides a method of local administration of one or more biologically active agents to a subject comprising in situ application of a composition comprising a mixture comprising D-Pep and/or D-L-Pep and at least one biologically active agent (D) in combination with D-Pep and/or D-L-Pep, described herein to the site of interest.

As used herein, the term "application" refers to the local in situ administration of the compositions of the present invention to the site of interest. The administration of the compositions of the present invention can be by any known means for contacting the hydrogel with the tissues of interest. Such means would include, for example, injection, spraying, swabbing, brushing, etc., the hydrogel compositions to the tissues.

In an exemplary embodiment, the compositions of the present invention are used after surgical resection of a tumor in a subject. The compositions are applied to the tissue margins and surrounding tissues after removal of the tumor. The tissues are then surgically closed.

Without being held to any particular mechanism of action, the compositions of the present invention allow for the sustained release of biologically active agents into the surrounding tissues post-operatively to enhance the effectiveness of the surgical treatment by local chemotherapeutic action on any remaining tumor cells which evaded surgical resection. The biologically active agents will be release from the hydrogel through dissolution and through the biodegradation of the hydrogel and the bonds between the Pep and D and linkers (L), to allow diffusion of D to come into contact with the surrounding tissues.

An advantage of the compositions and methods described herein is the fact that the use of local administration, allows for high concentrations of D at the site of the tumor without having systemic effects in the subject.

Another advantage of the compositions and methods described herein is the ability to provide chemotherapy in a sustained release formulation, in parts of the body where there would otherwise be limited access of the biologically active agent to the site of interest. For example, the brain is well known for the blood-brain barrier preventing hydrophobic and polar molecules from entering the brain tissues. Systemic doses of chemotherapeutic agents do not typically cross the barrier without other measures or formulations which can cause systemic toxicities. However, application of the compositions of the present invention directly into the brain after tumor resection, avoids this common problem.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated. By way of example, and not intending to limit the invention, the dose of the pharmaceutical compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the pharmaceutical compositions of the present invention can be at a concentration from about 1 nM to about 10,000 nM, preferably from about 10 nM to about 5,000 nM, more preferably from about 100 nM to about 500 nM.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

In accordance with an embodiment of the present invention, the medicament for treating a disease in a subject can encompass many different formulations known in the pharmaceutical arts, including, for example, intravenous and sustained release formulations. With respect to the inventive methods, the disease can include cancer. Cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

In another embodiment, the term "administering" means that at least one or more pharmaceutical compositions of the present invention are introduced locally to a site in a subject, preferably a subject receiving treatment for a disease, and the at least one or more compositions are allowed to come in contact with the one or more disease related cells or population of cells.

As used herein, the term "treat," as well as words stemming therefrom, includes diagnostic and preventative as well as disorder remitative treatment.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

In certain embodiments, the subject compositions comprise about 1% to about 75% or more by weight of the total composition, alternatively about 2.5%, 5%, 10%, 20%, 30%, 40%, 50%, 60% or 70%, of a biologically active agent.

The "therapeutically effective amount" of the pharmaceutical compositions to be administered will be governed by such considerations, and can be the minimum amount necessary to prevent, ameliorate or treat a disorder of interest. As used herein, the term "effective amount" is an equivalent phrase refers to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease, such as cancer.

In accordance with another embodiment, the present invention provides methods of treating cancer in a subject comprising administering to the mammal a therapeutically effective amount of the composition of the present invention sufficient to slow, stop or reverse the cancer in the subject.

It will be understood by those of skill in the art that the methods for making the compositions of the present invention can use any known solvents or mixtures thereof that will dissolve the chemotherapeutic agent. Moreover, other linkers can be used in the inventive methods to prepare the drug amphiphiles of the present invention. Known methods for extraction of the mixtures and drying can also be used.

These and other aspects of the present invention will be further appreciated upon consideration of the following Examples, which are intended to illustrate certain particular embodiments of the invention but are not intended to limit its scope, as defined by the claims.

EXAMPLES

Chemicals. All amino acids and Fmoc-Arg(pbf)-Wang Resin were purchased from AAPPTEC (Louisville, Ky.). Paclitaxel was from Ava Chem Scientific (San Antonio, Tex.), 4-bromobutyric acid, thiourea and palmitic acid (C16) were purchased from Sigma-Aldrich (St. Louis, Mo.). N,N'-diisopropylcarbodiimide (DIC) and 4-dimethylaminopyridine (DMAP) were obtained from TCI. 1,2-Ethanedithiol (EDT) was purchased form Alfa Aesar (Ward Hill, Mass.), and all other reagents and solvents were sourced through VWR.

AcFFFRGDR-OH (SEQ ID NO: 1) and AcCVVVRGDR-OH (SEQ ID NO: 2) peptide synthesis.

The peptide AcCFFFRGDR-OH (SEQ ID NO: 6) and AcCVVVRGDR-OH (SEQ ID NO: 5) were synthesized using AAPPTEC Focus XC synthesizer via standard Fmoc-solid phase technique. Fmoc groups were deprotected using 20% 4-methylpiperidine in DMF, and amino acid/HBTU/DIEA (4/3.98/6) was applied for coupling. The N-terminal amine was acetylated manually by reacting with 20% acetic anhydride in DMF. The finished peptides were cleaved from the resin with TFA/TIS/EDT/water (90:5:2.5:2.5) solution. The peptide AcCFFFRGDR-OH (SEQ ID NO: 6) and AcCVVVRGDR-OH (SEQ ID NO: 5) were confirmed by MALDI-TOFMS (FIGS. 4, 5). AcCFFFRGDR-OH (SEQ ID NO: 6): m/z 1089.6 for $[M+H]^+$, 564.3 for $[M+2Na]^{2+}$, $C_{50}H_{68}N_{14}O_{12}S$, calcd. 1089.2; AcCVVVRGDR-OH (SEQ ID NO: 5): m/z 1002.6 for $[M+H]^+$, 522.9 for $[M+2Na]^{2+}$, 501.9 for $[M+2H]^{2+}$, 347.8 for $[M+2Na+H]^{3+}$, $C_{40}H_{71}N_{15}O_{13}S$, calcd. 1002.2.

C16-FFFRGDR Synthesis.

Figures 6A, 6B:
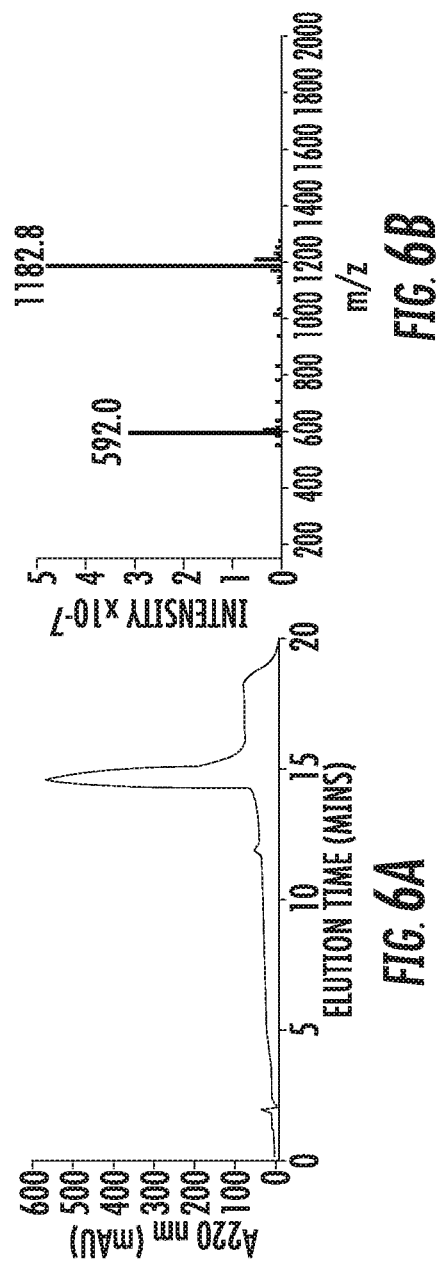
FIGS. 6A-6B show graphs depicting RP-HPLC trace (A) and MALDI-TOF MS (B) profile of conjugate C16-FFFRGDR (SEQ ID NO: 1) showing high purify and the expected molecular mass.

The peptide conjugate C16-FFFRGDR (SEQ ID NO: 1) was synthesized using same method as previous reported. The N-terminal amine was reacted with C16/HBTU/DIEA (4/3.98/6) for coupling. The finished peptide conjugate was cleaved from the resin with TFA/TIS/water (95:2.5:2.5) solution. The conjugate C16-FFFRGDR (SEQ ID NO: 1) was confirmed by MALDI-TOFMS m/z 1182.8 for $[M+H]^+$, 592.0 for $[M+2H]^{2+}$, $C_{61}H_{91}N_{13}O_{11}$, calcd. 1181.7 (FIG. 6).

Transmission Electron Microscopy.

All the self-assembly experiments were performed at room temperature. All conjugates was directly dissolved into deionized water to make solutions of desired concentrations. Solutions were typically aged for 24 h before TEM imaging. TEM samples were prepared by adding ~10 μL solution onto a carbon-film-coated copper grid. After careful removal of the excess liquid using a piece of filter paper, a drop of 2% w/v uranyl acetate aqueous solution (~10 μL) was added onto the TEM grid as a negative staining agent. Again, excess solution was removed using a piece of paper to result in a thin film on the grid that was allowed to air dry before imaging. A Technai12 TWIN transmission electron microscope was used to image the prepared samples operating typically at 100 kV, with images recorded by a SIS Megaview III wide-angle CCD camera.

Circular Dichroism (CD) Spectroscopy.

CD spectra were recorded on a Jasco J-710 spectropolarimeter (JASCO, Easton, Md.) using a 10 mm pathlength Spectrasil® quartz UV-Vis absorption cell (Starna Cells Inc., Atascadero, Calif.). Data was normalized with respect to sample concentration and path length.

Cell Lines.

U87 human glioblastoma cells were provided by Prof. Denis Wirtz's lab (Department of Chemical and Biomolecular Engineering, Johns Hopkins University). Primary human brain cancer cell line 965 was provided by Prof. Alfredo Quinones-Hinojosa of the Johns Hopkins Medical School. All cell lines were cultured according to providers' protocols. U87 human glioblastoma cells were grown in DMEM with 10% FBS and 1% antibiotics. Primary human brain cancer cell line 965 was grown in DEME/F12 with 2% Neuroplex, 1% antibiotics, 20 ng/mL hEGF and 20 ng/mL hFGF.

Cell Viability Study of Three Amphiphiles.

The cytotoxicity assays of PTX-FFFRGDR (SEQ ID NO: 1), PTX-VVVRGDR (SEQ ID NO: 2), C16-FFFRGDR (SEQ ID NO: 1) were determined using a dose-response study. A 96-well plate was seeded with cell sat a density of $5\times10^3$ cells/well and incubated at 37° C. for 24 h. The cells were then treated with varying concentrations of paclitaxel or conjugate in cell medium and incubated for a further 48 h (U87) or 72 h (primary cell lines). Cell viability was determined by sulforhodamine-B (SRB, Sigma Aldrich) assay according to the manufacturer's protocol. The data was fitted using the Hill equation function within the Igor Pro program and used to obtain the $IC_{50}$ value.

Tissue Organotypic-Glioblastoma Multiforme (GBM) Invasion Model.

Tumor tissue from GBM patients is collected in the operating room, from which single primary-derived cells are obtained and labeled with GFP. Tumor tissue can also be sliced in 150-300 μm slices and kept alive for 2 weeks in a semiporous membrane fed with media from the bottom (organotypic tissue). GBM-GFP tagged cells can be injected on the surface of the organotypic slices ($1\times10^5$ cells) and invade the tissue slices. 24 h after invasion of the GBMs 4 μl of drug amphiphile hydrogel are placed on top of the tissue. Imaging is then performed to measure the GBM-GFP tagged cells invading the normal tissue on the slide (FIG. 20).

In vivo brain tumor resection model to evaluate the drug amphiphile nanofiber hydrogels.

Figure 21A:
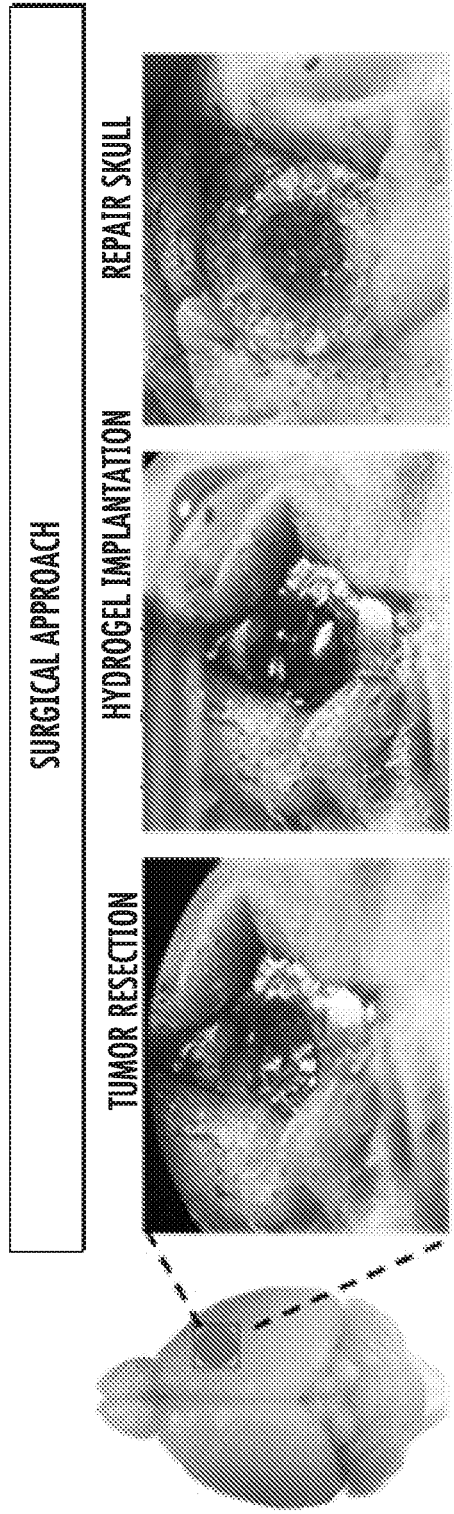
FIGS. 21A-21B depict an in vivo brain tumor resection model to evaluate the CPT nanofiber hydrogels. A) A cranial window (5 mm) was made at the same location of tumor implantation, and the tumor was resected with microscissors. A droplet of CPT nanofiber solution was placed in the resected area, forming hydrogels upon delivery. A methacrylate membrane was used to cover the skull defect. B) BLI analysis showed tumor growth and recurrence after 1 week of surgical resection, resembling the clinical conditions of GBM in humans.
Figure 21B:
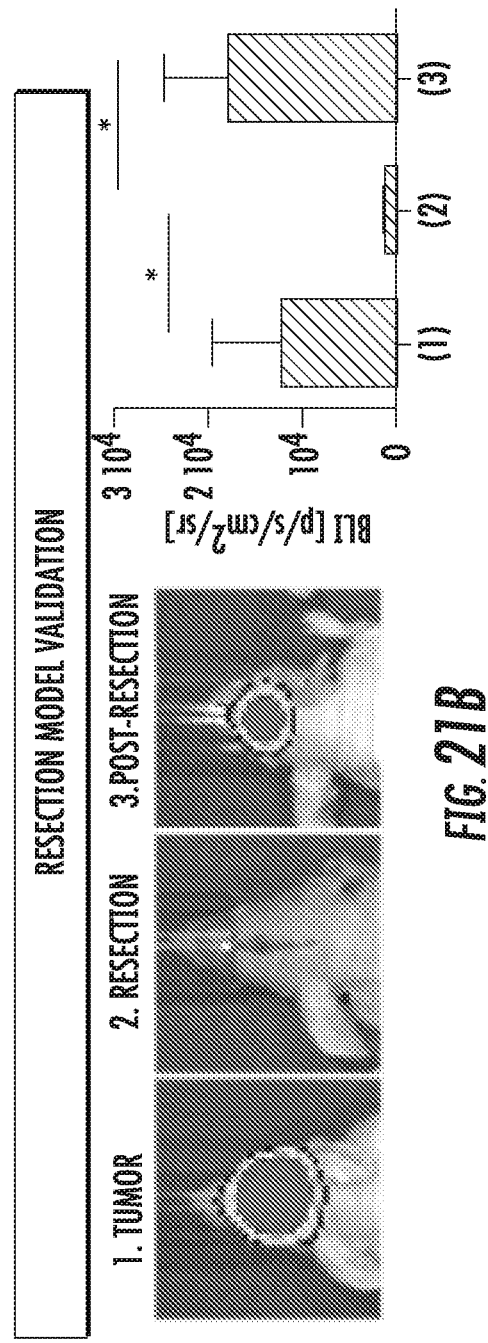

As shown in FIG. 21, a cranial window (5 mm) was made in a mouse at the same location of tumor implantation, and the tumor was resected with microscissors. A droplet of CPT-HKD nanofiber solution was placed in the resected area, forming hydrogels upon delivery. A methacrylate membrane was used to cover the skull defect. BLI analysis showed tumor growth and recurrence after 1 week of surgical resection, resembling the clinical conditions of GBM in humans.

Example 1 diBum-FFFRGDR (SEQ ID NO: 1) was synthesized in two steps. In the first step, the peptide KFFFRGDR (SEQ ID NO: 4) was synthesized using AAPPTEC Focus XC synthesizer via standard Fmoc-solid phase technique. Fmoc groups were deprotected in each step using 20% 4-methylpiperidine in DMF, and amino acid/HBTU/DIEA (4/3.98/6) was applied for coupling. In the second step, bumetanide was conjugated at both backbone and side chain amino groups of N-terminus lysine (Bumetanide/HBTU/DIEA (8/7.96/12). The finished conjugate was cleaved from the resin using a mixture of TFA/TIS/water (92.5:5:2.5) solution. The conjugate was confirmed by ESI MS m/z for 883.3 [M+2H], 1765.1 [M+H], $C_{85}H_{109}N_{19}O_{19}S_2$, calcd. 1765.0.

The compound diBum-FFFRGDR (SEQ ID NO: 1) was prepared, wherein two bumetanide molecules were linked to the Pep moiety via a lysine amino acid linker. Samples of the compound were run on reverse-phase HPLC and ESI-MS which shows high purity of the compound and the expected molecular mass (FIG. 7). $C_{16}$-Bum-FFFRGDR (SEQ ID NO: 1) was dissolved in DI water at 5 mM and aged for 24 hours. After 24 hours of aging, PBS buffer was added to trigger hydrogel formation. TEM images revealed nanofibers formation with diameter around 10 nm (FIG. 8).

Example 2

Ver-RGDR was synthesized in two steps. In the first step, the peptide RGDR (SEQ ID NO: 3) was synthesized using AAPPTEC Focus XC synthesizer via standard Fmoc-solid phase technique. Fmoc groups were deprotected using 20% 4-methylpiperidine in DMF, and amino acid/HBTU/DIEA (4/3.98/6) was applied for coupling. In the second step, verteporfin (Ver) was conjugated onto the backbone amino groups of N-terminus arginine (Verteporfin/HBTU/DIEA (4/3.98/6). The finished conjugate was cleaved from the resin with TFA/TIS/water (92.5:5:2.5) solution. The conjugate was confirmed by ESI MS m/z for 401.4 [M+3H], 601.9 [M+2H], 1202.7 [M+H], $C_{59}H_{74}N_{14}O_{14}$, calcd. 1203.3.

Figure 9:
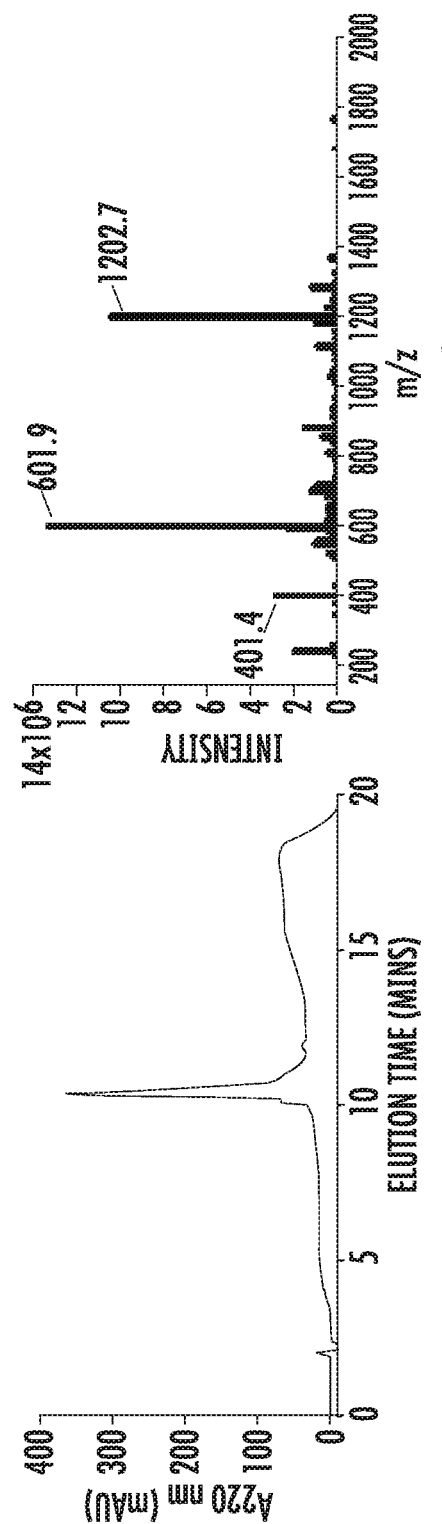
FIGS. 9A-9B show graphs depicting RP-HPLC trace (A) and ESI MS (B) profile of Ver-RGDR showing high purity and the expected molecular mass.
Figure 10:
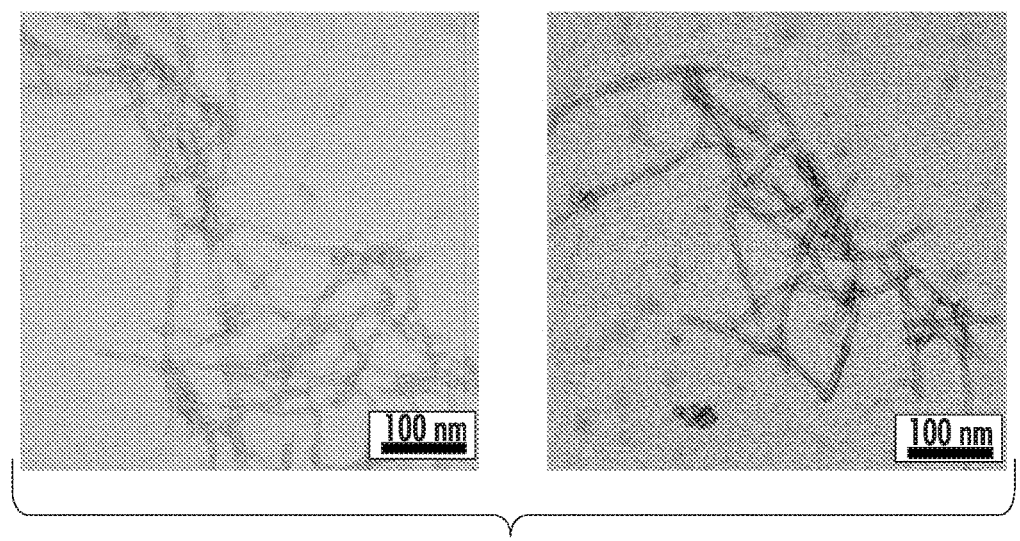
FIG. 10 is a pair of TEM images where Ver-RGDR was dissolved in DI water at 5 mM. After 24 aging, PBS buffer was added to trigger hydrogel formation. Short fibrous structures were observed in TEM images.

The compound Ver-RGDR was prepared, wherein the verteporfin molecule was linked directly to the RGDR (SEQ ID NO: 3) target (T) moiety via an amide bond. Samples of the compound were run on reverse-phase HPLC and ESI-MS which shows high purity of the compound and the expected molecular mass (FIG. 9). Ver-RGDR was dissolved in DI water at 5 mM and aged for 24 hours. After 24 hours of aging, short fibrous structures were observed in TEM images (FIG. 10).

Example 3

Figure 11A:
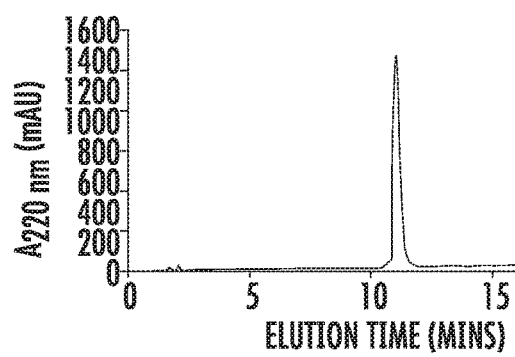
FIGS. 11A-11B show graphs depicting RP-HPLC trace (A) and ESI MS (B) profile of an embodiment of the present invention where D is paclitaxel (PTX), conjugated to Pep (VVVRGDR) (SEQ ID NO:2) as PTX-VVVRGDR showing high purity and the expected molecular mass.
Figure 11B:
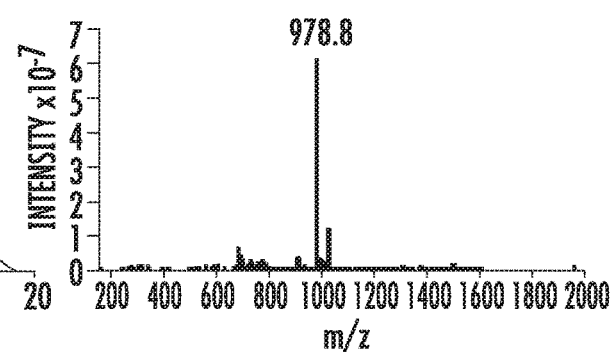

PTX-FFFRGDR (SEQ ID NO: 1) and PTX-VVVRGDR (SEQ ID NO: 2) were synthesized in three steps. In the first step, the peptide AcCVVVRGDR-OH (SEQ ID NO: 5) was synthesized as described above. In the second step, 4-(pyridin-2-yldisulfanyl) butyric acid and paclitaxel C2' ester was synthesized using the following method: 4-Bromobutyric acid (2 g, 12 mmol) and thiourea (0.96 g, 12.6 mmol) were dissolved in ethanol (50 mL) and refluxed at 90° C. for 4 h. After dropwise addition of a NaOH solution (4.8 g in 5:1 $H_2O$/ethanol), the mixture was refluxed for another 16 h and then cooled to room temperature. The white precipitate was collected and redissolved in water (40 mL). 4 M HCl was used to adjust the solution pH to 5, and the product was extracted into diethyl ether. The organic phase was dried over anhydrous sodium sulfate to give 4-sulfanylbutyric acid as a colorless oil (310 mg, 15%), which was used in the next step without further purification. 4-sulfanylbutyric acid (105 mg, 0.87 mmol) and 2-aldrithiol (440 mg, 2.0 mmol, 2.3 eq) were dissolved in MeOH (1.3 mL) and stirred for 3 h. The solution was purified by RP-HPLC (5% to 95% of acetonitrile in water with 0.1% TFA over 45 min), combining product fractions and removing solvents to give 4-(pyridin-2-yldisulfanyl) butyric acid as an oil (118 mg, 59%). Paclitaxel C2' ester was synthesized using a previously published procedure. Paclitaxel (186 mg, 0.22 mmol), 4-(pyridin-2-yldisulfanyl)butyric acid (100 mg, 0.44 mmol), DIC (68 μL, 0.44 mol), and DMAP (26.7 mg, 0.22 mmol) were added into an oven dried flask equipped with a stirrer bar, evacuated and refilled with nitrogen three times to remove air, then dissolved in anhydrous acetonitrile (12.7 mL). The reaction was allowed to stir in the dark at room temperature for 48 h. The solvents were removed in vacuo and the residue was dissolved in chloroform and purified by flash chromatography (3:2 EtOAc/hexane), to give the product as a white solid (108 mg, 47%). In the third step, AcCFFFRGDR (SEQ ID NO: 6) (5.0 mg, 4.6 μmol) and paclitaxel C2' ester (9.8 mg, 9.2 μmol), or AcCVVVRGDR-OH (SEQ ID NO: 5) (5.0 mg, 5.0 μmol) and paclitaxel C2' ester (10.6 mg, 10.0 μmol) were added to an oven dried flask equipped with a stirrer bar and evacuated and filled with nitrogen three times to remove the air. The reagents were then dissolved in anhydrous DMF (3 mL). The solution was allowed to stir for 16 h, before purification by RP-HPLC (5% to 95% acetonitrile in water with 0.1% TFA over 30 min). Product fractions were combined and lyophilized to give a PTX-FFFRGDR (SEQ ID NO: 1) and PTX-VVVRGDR (SEQ ID NO: 2) as white powders. PTX-FFFRGDR (SEQ ID NO: 1): ESI MS: m/z 1033.2 for [M+Na+H]2+, 1022.3 for [M+2H]2+, $C_{101}H_{123}N_{15}O_{27}S_2$, calcd. 2041.8; PTX-VVVRGDR (SEQ ID NO: 2): ESI MS: m/z 978.8 for [M+2H]2+, $C_{91}H_{126}N_{16}O_{28}S_2$, calcd. 1954.8 (FIGS. 11 and 13).

PTX-VVVRGDR (SEQ ID NO: 2) was dissolved in DI water/ACN (4:1) at 5 mM and aged under room temperature for 24 h. After 24 h aging, hydrogel was observed to form. ACN was removed by rotary evaporation, and hydrogel remain the same after aging for another 24 h. TEM images reveal dominant nanofibers as shown in FIG. 12.

Example 4

Transmission electron microscopy (TEM) imaging revealed that PTX-buSS-FFFRGDR (SEQ ID NO: 1) amphiphiles assemble into 1D twisting "super coil" nanofilaments in water (FIGS. 14A and 14B). At 5 mM, PTX-buSS-FFFRGDR (SEQ ID NO: 1) was observed to form filaments of 10.2±1.7 nm (n=10) with regular twisting pitch and lengths on the scale of hundreds of nanometers, and PTX-buSS-VVVRGDR (SEQ ID NO: 2) forms straight nanofibers of widths 12.5±1.3 nm (n=10) (FIG. 14C) that were predominantly longer than those formed by PTX-buSS-FFFRGDR (SEQ ID NO: 1). The negative control molecule, C16-FFFRGDR (SEQ ID NO: 1) with no bulky hydrophobic core, assembled into straight nanofibers as well, with widths 9.5±1.3 nm (n=10) and length in a few micrometers. The diameters of these nanofibers are approximately twice that of the expected molecular length (~4.9, 5.3 and 4.8 nm, respectively), indicating a cylindrical packing geometry of core-shell micelles.

Previous work has shown that the presence of short peptide sequences eases the formation of chiral β-sheets as secondary structure. For -FFF-containing peptides, large π-surfaces derived from aromatic side chains offer strong interactions among β-sheet peptides and bulky hydrophobic domains adjacent to paclitaxel segment, resulting in high rotational potential for twisting structures. It has been reported that concave aromatic system contributes effectively to the hierarchical growth of 3D helical fibers. Thus introduction of bulky paclitaxel drug domains with multi aromatic rings near the β-sheet-forming peptide sequences induces torsional strains in the secondary H-bonded nanostructure. On the other hand, amino acid side chains with one-handed helical chirality resulted in right-handed twisting of nanofibers upon elongation (indicated in FIG. 14B as arrows and dash lines). As a combination of twofold driving forces, PTX-buSS-FFFRGDR (SEQ ID NO: 1) with strong π-π interactions and bulky hydrophobic core assembled into "super coil" nanofilaments. The essential torsional strains from aromatic surfaces and bulky hydrophobic domains were further demonstrated by assembly behavior of PTX-buSS-VVVRGDR (SEQ ID NO: 2) and C16-FFFRGDR (SEQ ID NO: 1) with absence of it-surfaces and bulky drug domain, respectively. TEM images showed long and straight nanofibers with little twisting morphologies were formed under same conditions, confirming the leading role of both aromatic rings and bulky residues in these 1D assemblies.

Example 5

In order to further study gelation behavior of two paclitaxel amphiphiles, critical gelation concentrations (CGCs) were determined based on stable-to-inversion-of-a-test-tube method. Hydrogels of PTX-buSS-FFFRGDR (SEQ ID NO: 1) and PTX-buSS-VVVRGDR (SEQ ID NO: 2) were prepared under various concentrations from 1 mM to 5 mM. As shown in FIGS. 14E and 14F, PTX-buSS-FFFRGDR (SEQ ID NO: 1) formed viscous liquid at 2 mM while self-supported hydrogel was observed under 5 mM, indicating a CGC lying in-between. On the other hand, PTX-buSS-VVVRGDR (SEQ ID NO: 2) self-assembled into solid hydrogel at 2 mM and gel-sol transition occurred at 1 mM. The higher CGC of PTX-buSS-FFFRGDR (SEQ ID NO: 1) is resulted from shorter fiberlength and weaker inter-fiber crosslinking while straight and long filaments self-assembled from PTX-buSS-VVVRGDR (SEQ ID NO: 2) demonstrated much lower CGC between 1 mM and 2 mM.

Example 6

Figure 15A:
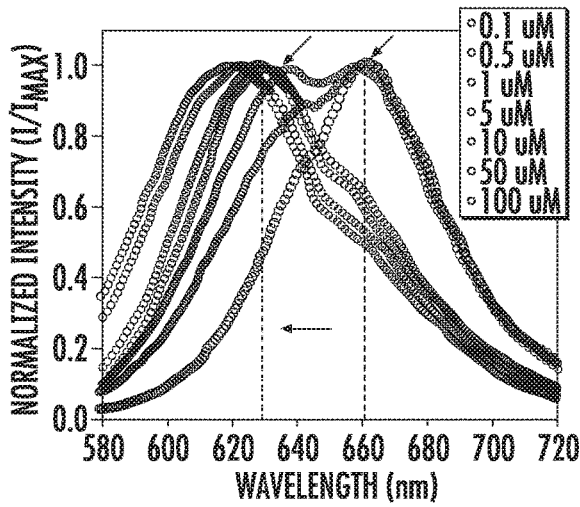
FIGS. 15A-15D illustrate fluorescence measurements to determine the CMC value of PTX-buSS-FFFRGDR (SEQ ID NO: 1) (A) and PTX-buSS-VVVRGDR (SEQ ID NO: 2) (B) based on Nile Red encapsulation within the assembled nanostructures. Representative CD spectra (solid lines) and UV-vis spectra (dash lines) of 200 µM PTX-buSS-FFFRGDR (SEQ ID NO: 1), 200 µM PTX-buSS-VVVRGDR (SEQ ID NO: 2) and 200 µM. C16-FFFRGDR (SEQ ID NO: 1) (C). Paclitaxel release study of PTX-buSS-FFFRGDR (SEQ ID NO: 1) and PTX-buSS-VVVRGDR (SEQ ID NO: 2) in PBS buffer at 37° C. at 50 µM. Solutions were incubated in the presence or absence of 10 mM GSH. Data are given as mean±s.d. (n=3).
Figure 15B:
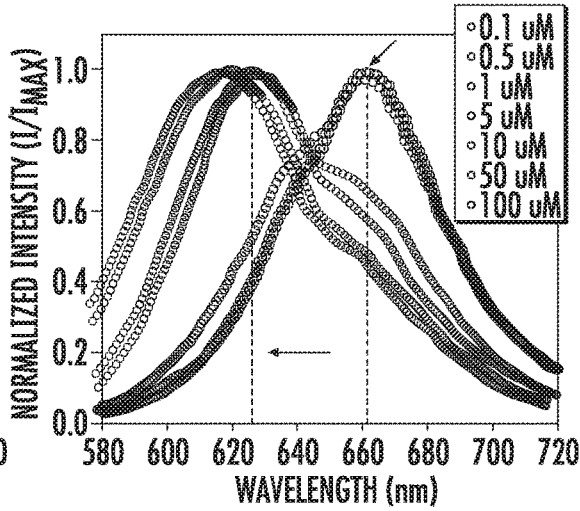
Figure 15C:
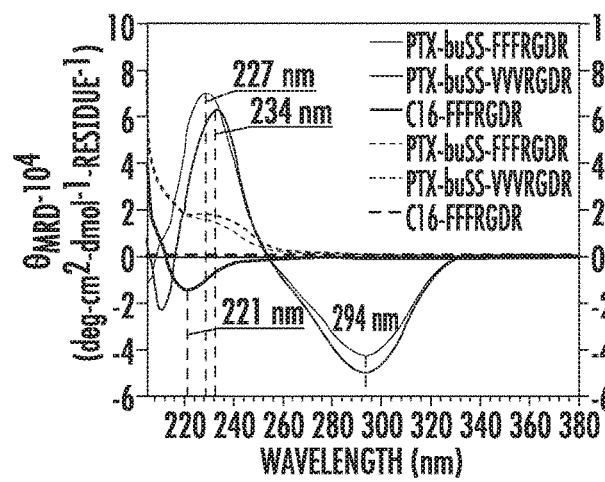

It is thought that the morphological differences of the observed nanostructures are resulted from phenylalanine residues in β-sheet peptides and paclitaxel domain. The β-sheet secondary structure was confirmed for each DA molecules by the observation of a negative signal around the 220 nm regions of the circular dichroism (CD) spectra (FIG. 15C). We found that the CD spectra of aqueous solutions of both PTX-buSS-FFFRGDR (SEQ ID NO: 1) and PTX-buSS-VVVRGDR (SEQ ID NO: 2) display strong signals in the PTX absorption regions at ~230 nm and 294 nm. The negative absorption at 294 nm with a shoulder at around 270 nm, and the positive absorption at 227 nm and 234 nm are all attributed to the PTX chromophores associated with different asymmetric centers. Previous study concluded that nearby phenylalanine rings led to significant transition of aromatic ring absorption, thus the blue shift of paclitaxel positive absorption may be the consequence of adjacent three phenylalanine side chains. FIG. 15 reveals the characteristic absorption of β-sheets at 221 nm for C16-FFFRGDR (SEQ ID NO: 1). It is likely that the β-sheets signal in PTX DAs is overwhelmed by strong absorption of paclitaxel.

Example 7

The critical micellization concentration (CMC) was evaluated using the solvatochromic fluorescent dye, Nile Red. Similar method has been reported in our previous work. Briefly, hydrophobic molecule Nile Red can partition into the hydrophobic compartment of assembled nanostructure, leading to changes in both fluorescence intensity and emission maximum. FIGS. 15A and 15B show plots of PTX DAs concentration versus Nile Red fluorescence intensity and maximum emission wave-length, suggesting both CMC values lying between 1 μM and 5 μM. Interestingly, PTX-buSS-FFFRGDR (SEQ ID NO: 1) demonstrated comparable fluorescence intensity at both 660 and 630 nm under 1 μM, revealing a considerable aggregation of drug amphiphiles. On the other hand, fluorescence intensity at 660 nm is significantly dominant under 1 μM for PTX-buSS-VVVRGDR (SEQ ID NO: 2), indicating prodrugs remaining in aqueous solution as non-aggregating molecules. Such a difference in fluorescence intensity under same concentration demonstrated self-assembly potential variety of two PTX DAs. Since PTX-buSS-FFFRGDR (SEQ ID NO: 1) obtains stronger driving forces from hydrophobic interaction of paclitaxel, π-π interactions from phenylalanine residues, and different hydro-gen bond strength affected by aromatic side chains, PTX-buSS-FFFRGDR (SEQ ID NO: 1) molecules assembled into nanostructures at lower concentration, leading to a more stable morphology under same conditions.

Example 8

Figure 15D:
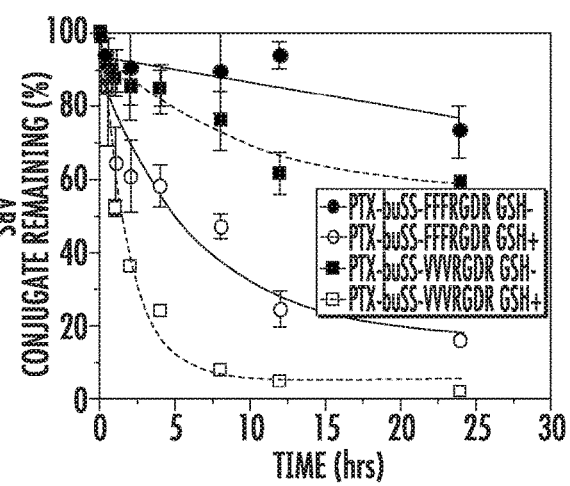

Since the release of the active compound is critical and tunable by altering nanofilaments morphologies, experiments to determine PTX release were carried out in PBS buffer at 37° C. in the presence or absence of 10 mM GSH (FIG. 15D). As expected, both DAs showed faster release rates under GSH conditions, in which both GSH and hydrolysis of the PTX ester bond are responsible for the release. However, under both GSH+ and GSH− conditions, PTX-buSS-FFFRGDR (SEQ ID NO: 1) showed a sustainable release rate compared with PTX-buSS-VVVRGDR (SEQ ID NO: 2). Since the PTX-buSS-FFFRGDR (SEQ ID NO: 1) is expected to be more stable from CMC measurement, more impact molecular packing and stronger interactions among peptide amphiphiles play essential roles to prevent small molecules to penetrating into inner hydro-phobic cores in which both reaction sites are present.

Example 9

Figure 16A:
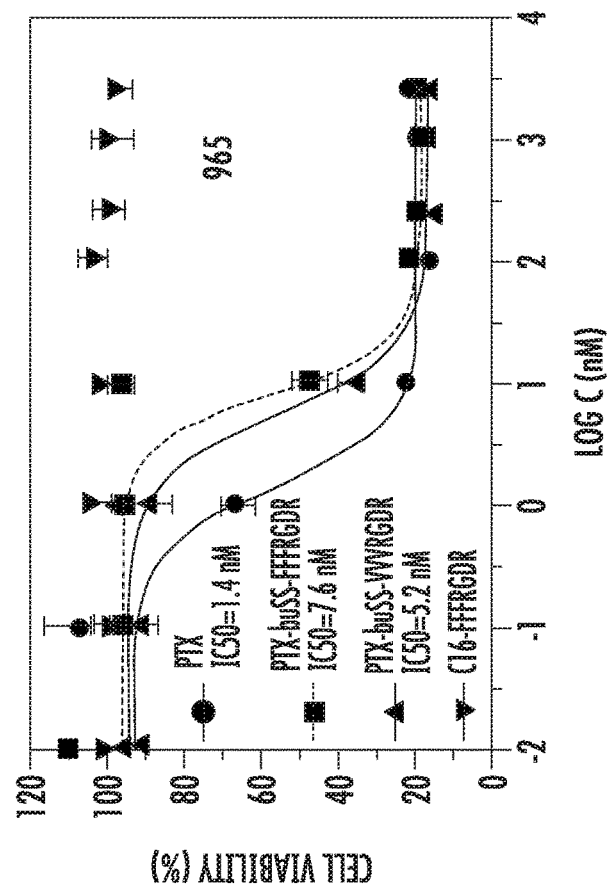
FIGS. 16A-16B depict the cytotoxicity evaluation of PTX-buSS-FFFRGDR (SEQ ID NO: 1), PTX-buSS-VVVRGDR (SEQ ID NO: 2), and C16-FFFRGDR (SEQ ID NO: 1) against U87 human glioblastoma cells (A) and 965 human primary brain tumor cells (B). Cells were incubated with the PTX or conjugates for 48 h (U87) or 72 h (965) and cell viability was determined by SRB assay. Data are given as mean±s.d. (n=3).
Figure 16B:
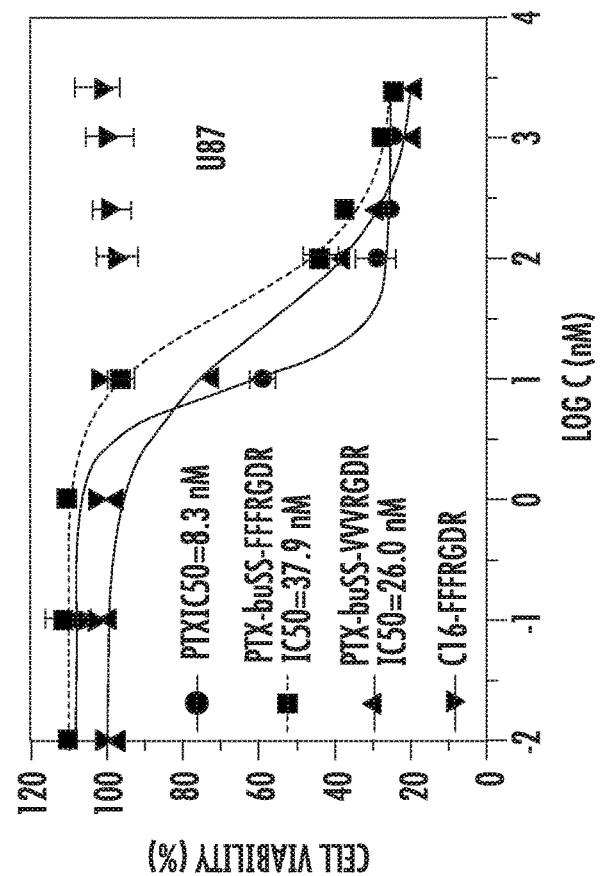

The in vitro cytotoxicity of PTX-buSS-FFFRGDR (SEQ ID NO: 1) was assessed an compared to that of free PTX, PTX-buSS-VVVRGDR (SEQ ID NO: 2) and C16-FFFRGDR (SEQ ID NO: 1) against two brain tumor cell lines, including U87 human glioblastoma cell line and 965 primary human brain tumor cell line (FIG. 16). Cells were incubated for 48 h with varying drug concentrations and cell viability was determined using sulforhodamine B (SRB) assay. For both brain tumor cell lines, PTX-buSS-FFFRGDR (SEQ ID NO: 1) and PTX-buSS-VVVRGDR (SEQ ID NO: 2) showed near-identical toxicity to free PTX, indicating that the conjugation of PTX to tumor-penetrating peptides does not compromise PTX's potency. On the other hand, C16-FFFRGDR (SEQ ID NO: 1) didn't show any significant toxicity against both cell line even under mM concentrations, revealing a biocompatibility and biosafety of peptide domains. Although paclitaxel prodrugs require a two-step release of bioactive PTX domain with first cleavage in cytosol by intracellular GSH and following hydrolysis, we expect our elegantly designed tumor penetrating peptide facilitated tumor cell binding and internalization, leading to a non-compromised accumulation of PTX DAs intracellularly.

Example 10

Figure 17A:
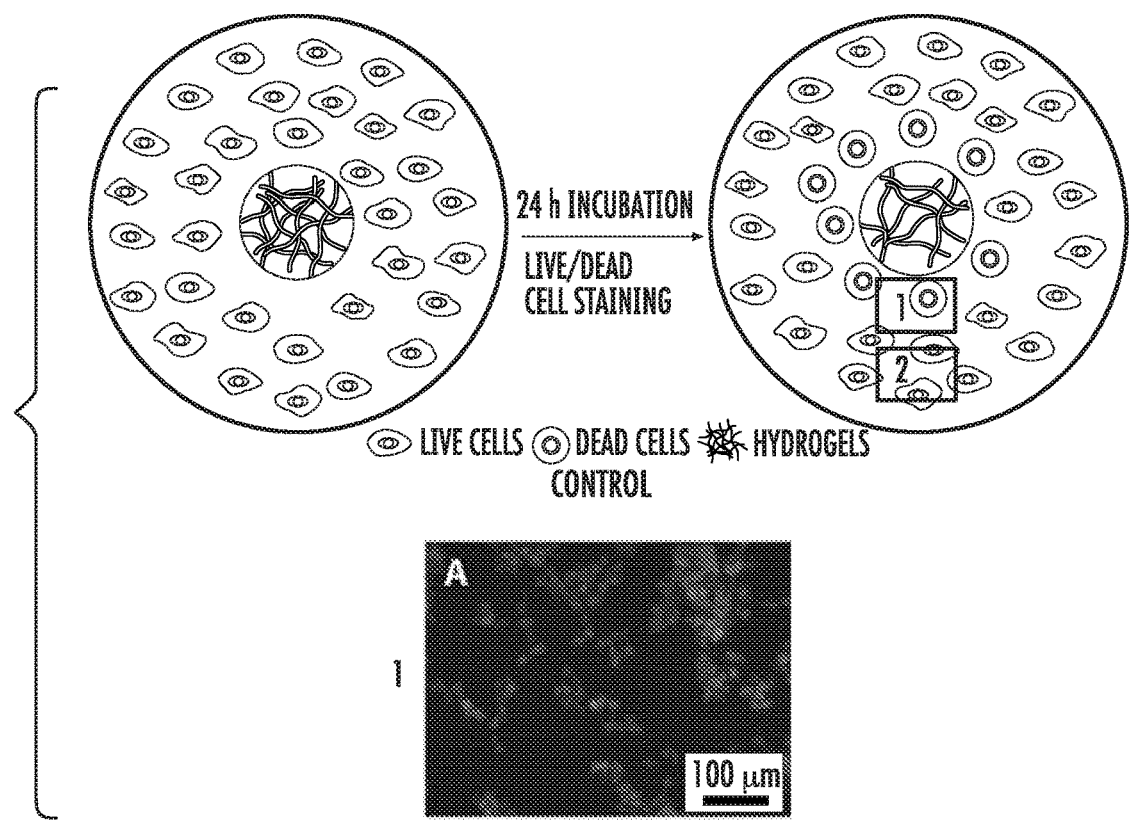
FIGS. 17A-17F show the in vitro drug release and cytotoxicity study of PTX-buSS-FFFRGDR (SEQ ID NO: 1), PTX-buSS-VVVRGDR (SEQ ID NO: 2), and C16-FFFRGDR (SEQ ID NO: 1) hydrogels against U87 human glioblastoma cells. Live/dead assay cell images after 24 h of incubation with blank culture media (A and D), PTX-buSS-FFFRGDR (SEQ ID NO: 1) (B and E), or C16-FFFRGDR (SEQ ID NO: 1) (C and F).
Figures 17B, 17C:
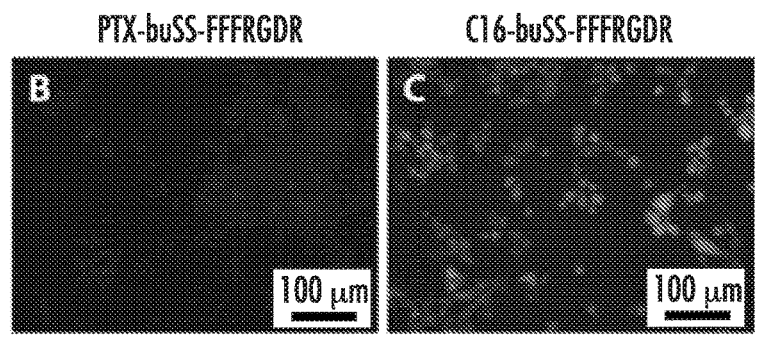
Figures 17D, 17E, 17F:
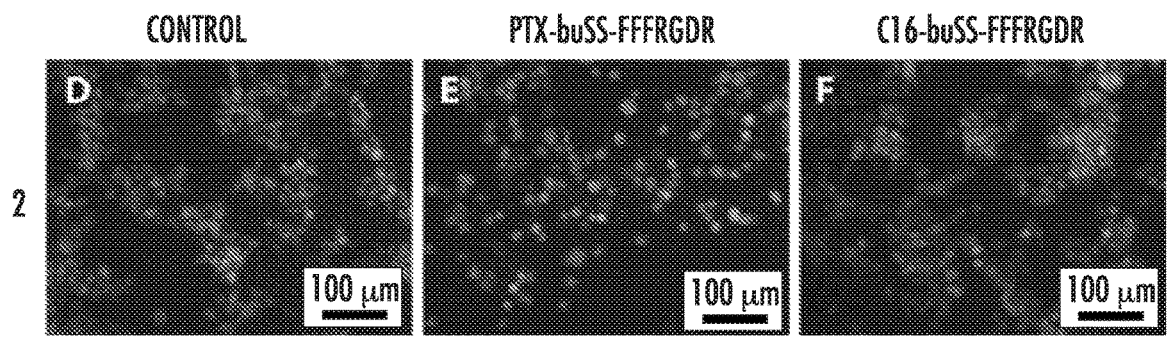

The in vitro drug release and cytotoxicity of PTX-buSS-FFFRGDR (SEQ ID NO: 1) was assessed and compared to that of C16-FFFRGDR (SEQ ID NO: 1) blank hydrogel against U87 human glioblastoma cells (FIG. 17). Cells were incubated for 24 h with PTX-loaded and PTX-free hydrogels and cell viability was determined using live/dead cell staining method. Two sections along gradient decaying radius were taken to compare cell viability after treatment with different hydrogels. The U87 cells treated by PTX-loaded hydrogels show intense red fluorescence in near-gel region 1 and mostly green fluorescence in peripheral region 2, indicating a decreasing DA concentration released from central hydrogel. The concentration gradient from hydrogel center to peripheral area further revealed its sustained chemotherapeutic agent release for long time scale local treatment. Contrarily, blank hydrogel C16-FFFRGDR (SEQ ID NO: 1) demonstrated non-toxicity against U87 cells in both regions, which is consistent with previous in vitro cytotoxicity study using SRB assay.

Example 11

Synthesis and Properties of CPT-GVVQQHKD (SEQ ID NO: 7) (CPT-HKD).

Figure 18A:
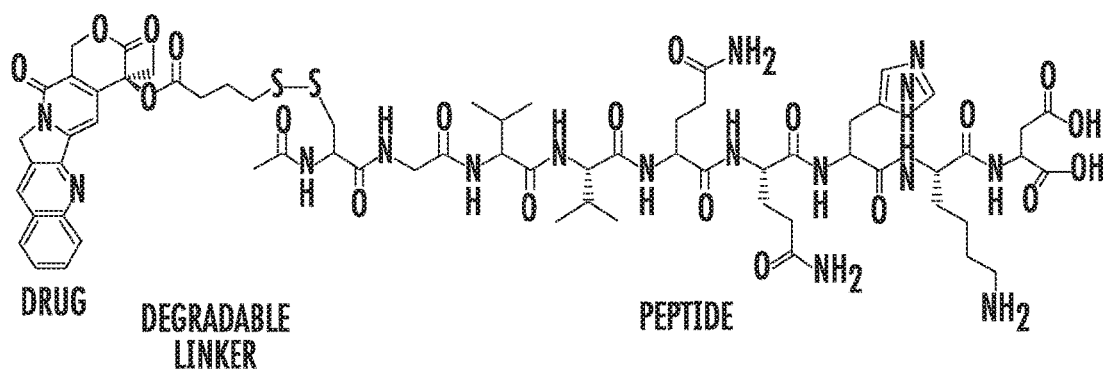
FIGS. 18A-18B show synthesized molecule CPT-buSS-GVVQQHKD (SEQ ID NO: 7) (CPT-HKD) as the new therapeutic drug amphiphile to treat malignant glioma. (A) The molecular structure of CPT-HKD, which contains camptothecin (CPT, labeled in blue), the buSS glutathione-cleavable linker (black), β-sheet forming peptide with a charged headgroup (green). (B) This CPT DA spontaneously associates into nanofibers with a width of around 10 nm, as evidenced by TEM. These CPT nanofibers form a hydrogel at a concentration higher than 0.4 wt % in DPBS. (C) Cumulative release of drug from the hydrogel formed by CPT-HKD (1.2 wt %) over one month. The hydrogel retained its shape after one month. (D) Cell viability of primary glioma cells derived from three patients treated by CPT-HKD of varying concentrations.
Figure 18B:
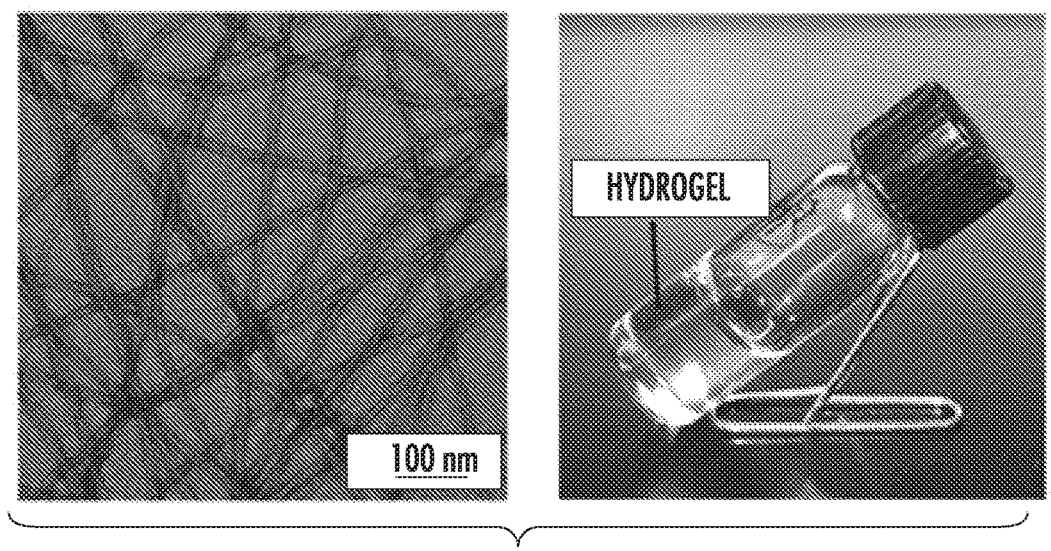
Figure 18C:
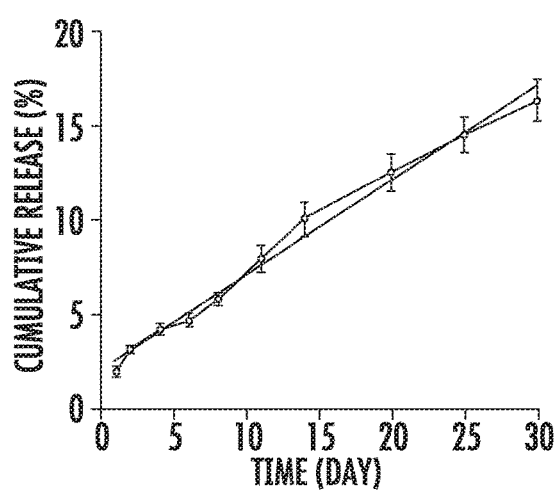
Figure 18D:
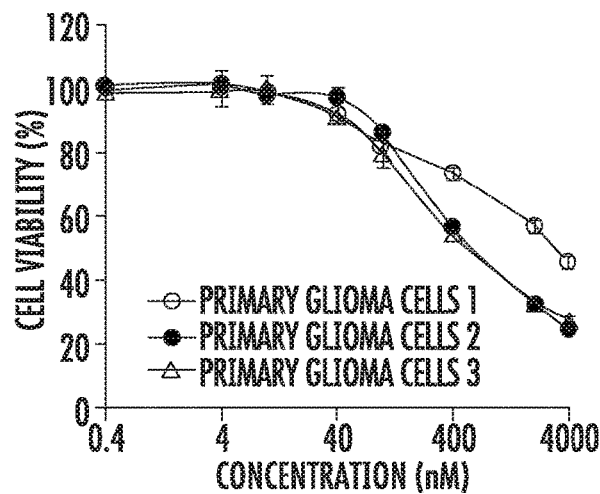

A drug amphiphiles comprising camptothecin (CPT) was conjugated to the Pep GVVQQHKD (SEQ ID NO: 7) with a buSS linker (CPT-buSS-GVVQQHKD) (FIG. 18A). This molecule was prepared for use as a new therapeutic hydrogelator to potentially treat malignant glioma. The molecular structure of CPT-HKD, which contains camptothecin (CPT, labeled in blue), the buSS glutathione-cleavable linker (black), β-sheet forming peptide with a charged headgroup (green) (FIG. 18A). The CPT-HKD drug amphiphile spontaneously associates into nanofibers with a width of around 10 nm, as evidenced by TEM (FIG. 18B). The CPT-HKD nanofibers form a hydrogel at a concentration higher than 0.4 wt % in DPBS. FIG. 18C shows the cumulative release of drug from the hydrogel formed by CPT-HKD (1.2 wt %) over one month, reaching levels of about 15% of total bound drug. The hydrogel retained its shape after one month. CPT-HKD was incubated with primary glioma cells derived from three patients to determine cytotoxicity (FIG. 18D). There was a dose dependent cytotoxicity shown in all three cell lines at varying concentrations.

The filamentous and gelation properties of CPT-HKD were also determined. FIGS. 19A-19C show the filamentous properties of CPT-HKD in water, DPBS and 50% FBS in DPBS.

Example 12

CPT-HKD Nanofiber Hydrogels were Shown to Suppress Tumor Growth and Prolong Survival.

Figure 22A:
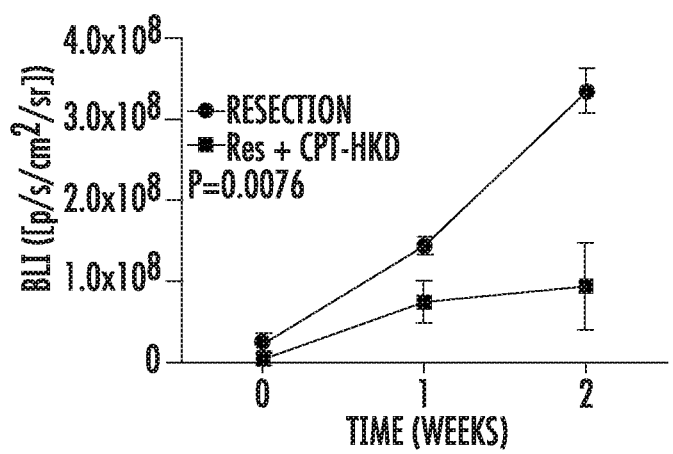
FIGS. 22A-22B show CPT-HKD nanofiber hydrogels suppress tumor growth and prolong survival. A) Signal quantification showed significant lower intensity in the treated group versus the resection only group was maintained over different time points (1 and 2 weeks, p=0.0076). B) Kaplan-Meier survival plot. Difference in survival between groups showed an extension of one-week in the CPT hydrogel treated mice compared to the resection only group (41 vs 35 days, respectively, quantification of n=4 animals per group, p=0.01).
Figure 22B:
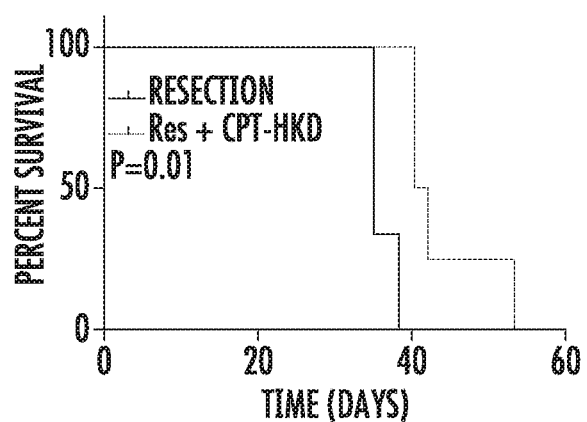

Using the in vivo brain tumor resection model described above, mice with implanted tumors were treated with resection of the tumor alone or resection and addition of CPT-HKD hydrogel and the tumor site was subjected to BLI analysis at 1 and 2 weeks post-resection. As shown in FIG. 22A, signal quantification showed significant lower intensity in the treated group versus the resection only group was maintained over different time points (1 and 2 weeks, p=0.0076). Kaplan-Meier analysis showed a difference in survival between groups showed an extension of one-week in the CPT hydrogel treated mice compared to the resection only group (41 vs. 35 days, respectively, quantification of n=4 animals per group, p=0.01).

Example 13

CPT Nanofiber Hydrogels Treatment Reduces Brain Tumor Area.

Using the in vivo brain tumor resection model described above, mice with implanted tumors were treated with resection of the tumor alone or resection and addition of CPT-HKD hydrogel for 1 month. After the test period, mouse brains were removed and sectioned in 10 μm thick sections and stained using H&E methods. Tumor area was determined by stereological analysis of consecutive 10 μm thick sections. p value was calculated by Mann-Whitney U (p=0.037). FIG. 23A shows a graph of the tumor area (mm$^2$) of control resection vs. CPY-HKD treatment. FIG. 23B shows H&E image examples from resection only and CPT treated mice. Scale bar: 1 mm.

Example 14

Figure 24A:
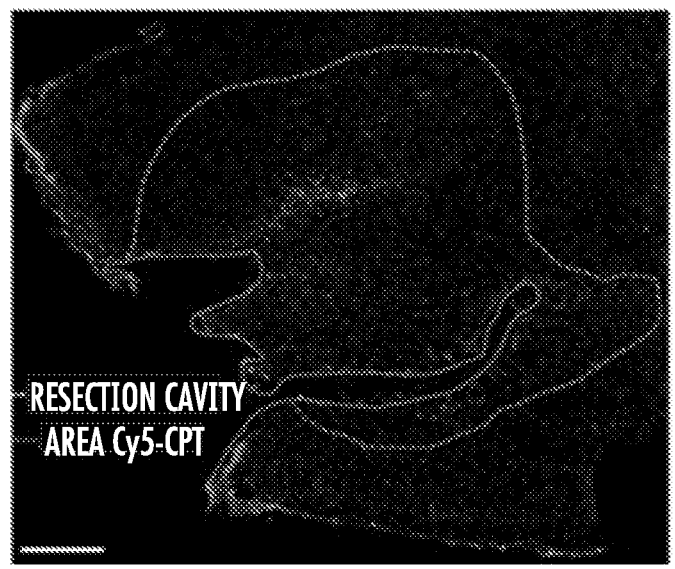
FIGS. 24A-24B show CY5-CPT hydrogel staining in vivo. a) The image depicts the diffusion of Cy5-CPT hydrogel into the mouse brain adjacent to the resection site. B) Quantification of CY5-CPT-HKD hydrogel area tissue penetration. Average area: 0.73 mm$^2$, SEM: 0.088. Scale bar: 0.25 mm.
Figure 24B:
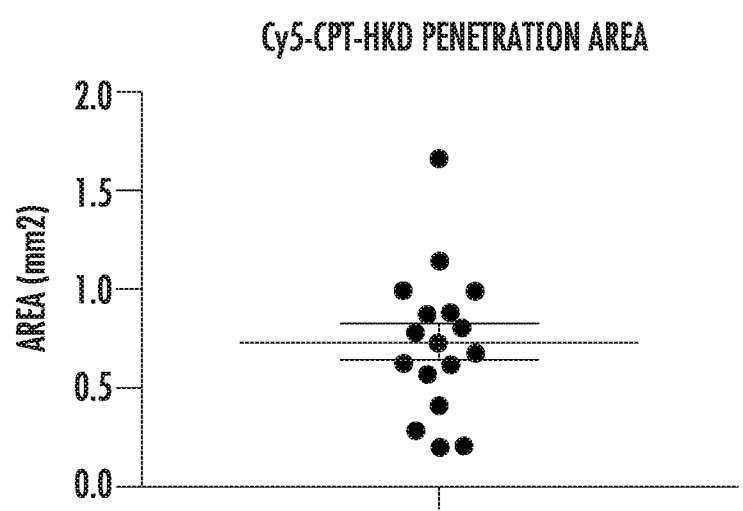

Using the in vivo brain tumor resection model described above, mice with implanted tumors were treated with resection of the tumor and addition of CPT-HKD hydrogel linked with CY5 fluorescent dye (CY5-CPT-HKD). FIG. 24 shows the diffusion of the CY5-CPT-HKD hydrogel into the mouse brain adjacent to the resection site and quantification of CY5-CPT-HKD hydrogel area tissue penetration. The average area of penetration was: 0.73 mm$^2$, SEM: 0.088. Scale bar: 0.25 mm.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A nanofiber hydrogel composition (D-Pep) comprising one or more biologically active agents (D) conjugated to a hydrophilic peptide composition (Pep), wherein D is selected from the group consisting of bumetanide, verteporfrin, vorapaxar, camptothecin and paclitaxel;
   wherein Pep is a hydrophilic peptide having an N and C terminal end and having the amino acid sequence GVVQQHKD (SEQ ID NO: 7).

2. The nanofiber hydrogel composition of claim 1, wherein D is one to four biologically active agents covalently linked to Pep.

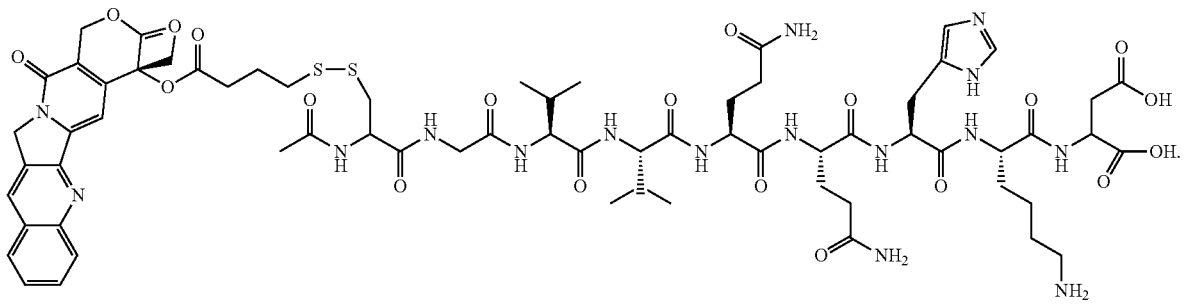

3. The composition of claim 1, wherein D is at least two different biologically active agents.

4. A nanofiber hydrogel composition comprising the composition of claim 1, and at least one additional biologically active agent in a mixture.

5. The nanofiber hydrogel composition of claim 4, wherein the at least one additional biologically active agent is a cancer chemotherapeutic drug.

6. The nanofiber hydrogel composition of claim 5, wherein the at least one additional biologically active agent is an alkylating agent, nitrogen mustard alkylating agent, nitrosourea alkylating agent, antimetabolite, purine analog antimetabolite, pyrimidine analog antimetabolite, hormonal antineoplastic, natural antineoplastic, antibiotic natural antineoplastis, vinca alkaloid natural antineoplastic, carboplatin, cisplatin, carmustine (BCNU), methotrexate, fluorouracil (5-FU), gemcitabine, goserelin, leuprolide, tamoxifen, aldesleukin, interleukin-2, docetaxel, etoposide, interferon, paclitaxel, other taxane derivatives, tretinoin (ATRA), bleomycin, dactinomycin, daunorubicin, doxorubicin, mitomycin, bumetanide, verteporfrin, vorapaxar, or camptothecin.

7. A method for treatment of cancer in a subject in need thereof comprising administering to the subject an effective amount of the composition of claim 1.

8. The method of claim 7, wherein the composition is administered to the subject after resection of a tumor from a selected tissue of the subject.

9. The method of claim 8, wherein the selected tissue of the subject is the brain.

10. The method of claim 9, wherein the tumor is a glioma.

11. A nanofiber hydrogel composition (D-L-Pep) comprising one or more biologically active agents (D) conjugated to a linker (L) which is conjugated to a hydrophilic peptide composition (Pep), wherein D is selected from the group consisting of bumetanide, verteporfrin, vorapaxar, camptothecin and paclitaxel;
   L is 1 to 4 biodegradable linkers; and
   Pep is a hydrophilic peptide having an N and C terminal end and having the amino acid sequence GVVQQHKD (SEQ ID NO: 7).

12. The nanofiber hydrogel composition of claim 11, wherein D is one to four biologically active agents covalently linked to Pep.

13. The composition of claim 11, which comprises

14. A method for treatment of cancer in a subject in need thereof comprising administering to the subject an effective amount of the composition of claim 11.

15. The method of claim 14, wherein the composition is administered to the subject after resection of a tumor from a selected tissue of the subject.

16. The method of claim 15, wherein the selected tissue of the subject is the brain.

17. The method of claim 16, wherein the tumor is a glioma.

18. A nanofiber hydrogel composition comprising the composition of claim 11, and at least one additional biologically active agent in a mixture.

19. The composition of claim 18, wherein the at least one additional biologically active agent comprises an imaging agent.

20. The nanofiber hydrogel composition of claim 18, wherein the at least one additional biologically active agent is a cancer chemotherapeutic drug.

21. The nanofiber hydrogel composition of claim 20, wherein the at least one additional biologically active agent is an alkylating agent, nitrogen mustard alkylating agent, nitrosourea alkylating agent, antimetabolite, purine analog antimetabolite, pyrimidine analog antimetabolite, hormonal antineoplastic, natural antineoplastic, antibiotic natural antineoplastis, vinca alkaloid natural antineoplastic, carboplatin, cisplatin, carmustine (BCNU), methotrexate, fluorouracil (5-FU), gemcitabine, goserelin, leuprolide, tamoxifen, aldesleukin, interleukin-2, docetaxel, etoposide, interferon, paclitaxel, other taxane derivatives, tretinoin (ATRA), bleomycin, dactinomycin, daunorubicin, doxorubicin, mitomycin, bumetanide, verteporfrin, vorapaxar, and camptothecin.

* * * * *

UNITED STATES PATENT AND TRADEMARK OFFICE
CERTIFICATE OF CORRECTION

PATENT NO. : 11,160,875 B2  
APPLICATION NO. : 15/736818  
DATED : November 2, 2021  
INVENTOR(S) : Honggang Cui and Alfredo Quinones-Hinojosa Page 1 of 1

It is certified that error appears in the above-identified patent and that said Letters Patent is hereby corrected as shown below:

In the Claims

Column 36, Claim 13, Line 13, it reads:

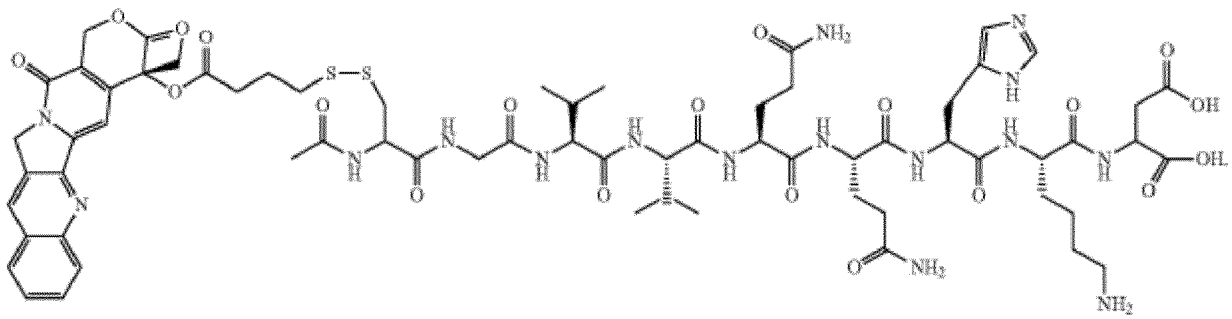

Whereas it should read:

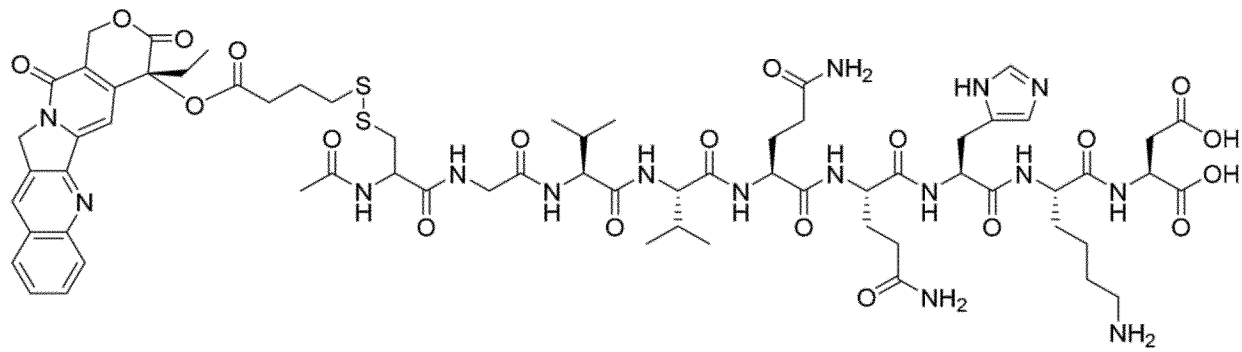

Signed and Sealed this  
Eighth Day of February, 2022

Drew Hirshfeld  
*Performing the Functions and Duties of the*  
*Under Secretary of Commerce for Intellectual Property and*  
*Director of the United States Patent and Trademark Office*